US011612331B2

(12) United States Patent
Wyeth et al.

(10) Patent No.: US 11,612,331 B2
(45) Date of Patent: Mar. 28, 2023

(54) HEADSET DEVICE FOR DETECTING FLUID IN CRANIUM VIA TIME VARYING MAGNETIC FIELD PHASE SHIFTS AND HARMONICS OF FUNDAMENTAL FREQUENCIES

(71) Applicant: Cerebrotech Medical Systems, Inc., Pleasanton, CA (US)

(72) Inventors: Richard Warren Wyeth, Discovery Bay, CA (US); Mitchell Elliott Levinson, Pleasanton, CA (US)

(73) Assignee: Cerebrotech Medical Systems, Inc., Pleasanton, CA (US)

( * ) Notice: Subject to any disclaimer, the term of this patent is extended or adjusted under 35 U.S.C. 154(b) by 666 days.

(21) Appl. No.: 16/446,954

(22) Filed: Jun. 20, 2019

(65) Prior Publication Data

US 2019/0365274 A1 Dec. 5, 2019

Related U.S. Application Data

(63) Continuation of application No. 14/690,985, filed on Apr. 20, 2015, now Pat. No. 10,335,054, which is a
(Continued)

(51) Int. Cl.
*A61B 5/0522* (2021.01)
*A61B 5/05* (2021.01)
(Continued)

(52) U.S. Cl.
CPC .......... *A61B 5/0522* (2013.01); *A61B 5/0037* (2013.01); *A61B 5/031* (2013.01);
(Continued)

(58) Field of Classification Search
CPC ...................... A61B 2562/0223; A61B 5/0522
See application file for complete search history.

(56) References Cited

U.S. PATENT DOCUMENTS 3,720,763 A 3/1973 Ishii
3,789,834 A 2/1974 Duroux
(Continued)

FOREIGN PATENT DOCUMENTS

AU 2015227382 B2 4/2017
CN 1158077 A 8/1997
(Continued)

OTHER PUBLICATIONS

European Search Report for Application No. 19181054.8, dated Oct. 28, 2019, 8 pages.
(Continued)

*Primary Examiner* — Serkan Akar
(74) *Attorney, Agent, or Firm* — Merchant & Gould P.C.

(57) ABSTRACT

A diagnostic method for monitoring changes in a fluid medium in a patient's head. The method includes positioning a transmitter at a first location on or near the patient's head, the transmitter generates and transmits a time-varying magnetic field into a fluid medium in the patient's head responsive to a first signal; positioning a receiver at a second location on or near the patient's head offset from the transmitter, the receiver generates a second signal responsive to a received magnetic field at the receiver; transmitting a time-varying magnetic field into the fluid medium in the patient's head in response to the first signal; receiving the transmitted magnetic field; generating the second signal responsive to the received magnetic field; and determining, a phase shift between the transmitted magnetic field and the received magnetic field for a plurality of frequencies of the transmitted time-varying magnetic field.

9 Claims, 10 Drawing Sheets

Related U.S. Application Data continuation of application No. 14/275,549, filed on May 12, 2014, now abandoned, which is a continuation of application No. 13/745,710, filed on Jan. 18, 2013, now Pat. No. 8,731,636.

(60) Provisional application No. 61/588,516, filed on Jan. 19, 2012.

(51) Int. Cl.
*A61B 5/00* (2006.01)
*A61B 5/03* (2006.01)
*G16H 50/30* (2018.01)
*G16H 50/20* (2018.01)

(52) U.S. Cl.
CPC .............. *A61B 5/05* (2013.01); *A61B 5/4064* (2013.01); *A61B 5/4839* (2013.01); *A61B 5/6803* (2013.01); *A61B 5/6814* (2013.01); *A61B 5/6831* (2013.01); *A61B 5/721* (2013.01); *A61B 5/7225* (2013.01); *A61B 5/7246* (2013.01); *A61B 5/7257* (2013.01); *A61B 5/7275* (2013.01); *A61B 5/7278* (2013.01); *A61B 5/7282* (2013.01); *G16H 50/20* (2018.01); *A61B 5/0042* (2013.01); *A61B 5/4848* (2013.01); *A61B 5/4875* (2013.01); *A61B 5/4878* (2013.01); *A61B 2560/0223* (2013.01); *A61B 2562/0223* (2013.01); *A61B 2562/166* (2013.01); *A61B 2562/182* (2013.01); *A61B 2562/222* (2013.01); *A61B 2576/026* (2013.01); *G16H 50/30* (2018.01)

(56) References Cited

U.S. PATENT DOCUMENTS

| | | | |
|---|---|---|---|
| 4,240,445 A | 12/1980 | Iskander | |
| 4,488,559 A | 12/1984 | Madgy | |
| 4,690,149 A | 9/1987 | Harvey | |
| 4,819,648 A | 4/1989 | Ko | |
| 5,001,436 A | 3/1991 | Scot | |
| 5,128,354 A | 7/1992 | Masuda | |
| 5,189,018 A | 2/1993 | Goldman | |
| 5,441,495 A | 8/1995 | Liboff et al. | |
| 5,446,384 A | 8/1995 | Dumoulin | |
| 5,617,861 A | 4/1997 | Ross et al. | |
| 5,827,893 A | 10/1998 | Lurie | |
| 5,853,370 A | 12/1998 | Chance | |
| 5,919,144 A | 7/1999 | Bridger | |
| 6,102,905 A | 8/2000 | Baxter et al. | |
| 6,126,595 A | 10/2000 | Amano et al. | |
| 6,356,081 B1 | 3/2002 | Misic | |
| 6,413,227 B1 | 7/2002 | Yost | |
| 6,723,047 B1 | 4/2004 | Yamamoto | |
| 6,924,773 B1 | 8/2005 | Paratte | |
| 7,122,012 B2 | 10/2006 | Bouton | |
| 7,251,521 B2 | 7/2007 | Seeber | |
| 7,638,341 B2 | 12/2009 | Rubinsky | |
| 7,910,374 B2 | 3/2011 | Rubinsky | |
| 7,998,080 B2 | 8/2011 | Ben-Ari et al. | |
| 8,101,421 B2 | 1/2012 | Rubinsky | |
| 8,109,899 B2 | 2/2012 | Sundstrom | |
| 8,303,110 B1 | 11/2012 | Weaver et al. | |
| 8,361,391 B2 | 1/2013 | Rubinsky | |
| 8,506,514 B2 | 8/2013 | Pedersen | |
| 8,731,636 B2 | 5/2014 | Wyeth | |
| 8,808,190 B2 | 8/2014 | Rosell Ferrer et al. | |
| 9,307,918 B2 | 4/2016 | Kinrot et al. | |
| 9,357,970 B2 | 6/2016 | Clark et al. | |
| 9,456,757 B1 | 10/2016 | Zheng | |
| 10,335,054 B2 | 7/2019 | Wyeth | |
| 10,743,815 B2 | 8/2020 | Wyeth et al. | |
| 11,166,671 B2 | 11/2021 | Levinson et al. | |
| 2001/0034478 A1 | 10/2001 | Lambert | |
| 2003/0191409 A1 | 10/2003 | Yost | |
| 2003/0199784 A1 | 12/2003 | Lenhardt | |
| 2005/0054939 A1 | 3/2005 | Ben-Ari et al. | |
| 2005/0065422 A1 | 3/2005 | Kandor | |
| 2005/0107685 A1 | 5/2005 | Seeber | |
| 2005/0119716 A1 | 6/2005 | McClure | |
| 2006/0116600 A1 | 6/2006 | Vesely et al. | |
| 2007/0032827 A1 | 2/2007 | Katims | |
| 2008/0177163 A1 | 7/2008 | Wang et al. | |
| 2008/0183064 A1 | 7/2008 | Chandonnet et al. | |
| 2008/0224688 A1 | 9/2008 | Rubinsky et al. | |
| 2009/0105605 A1 | 4/2009 | Abreu | |
| 2009/0234245 A1 | 9/2009 | Jaffe et al. | |
| 2010/0021035 A1 | 1/2010 | Gupta et al. | |
| 2010/0030293 A1 | 2/2010 | Sarkar | |
| 2010/0277163 A1 | 11/2010 | Nakamura et al. | |
| 2011/0193575 A1 | 8/2011 | Rubinsky | |
| 2011/0267074 A1 | 11/2011 | Xie | |
| 2012/0083717 A1 | 4/2012 | Alleman et al. | |
| 2012/0101326 A1 | 4/2012 | Simon | |
| 2012/0203134 A1 | 8/2012 | Kinrot et al. | |
| 2012/0245442 A1 | 9/2012 | Ukawa | |
| 2013/0187666 A1 | 7/2013 | Rubinsky | |
| 2013/0190599 A1 | 7/2013 | Wyeth | |
| 2013/0274615 A1 | 10/2013 | Ben-Ari | |
| 2014/0243647 A1 | 8/2014 | Clark | |
| 2014/0249400 A1 | 9/2014 | Wyeth | |
| 2014/0371545 A1 | 12/2014 | Ben-Ari | |
| 2015/0209174 A1 | 7/2015 | Abreu | |
| 2015/0313496 A1 | 11/2015 | Connor | |
| 2015/0374292 A1 | 12/2015 | Wyeth | |
| 2016/0007879 A1 | 1/2016 | Gonzalez | |
| 2016/0310054 A1 | 10/2016 | Izzetoglu et al. | |
| 2017/0055839 A1 | 3/2017 | Levinson | |
| 2017/0127946 A1 | 5/2017 | Levinson | |
| 2017/0319099 A1 | 11/2017 | Levinson | |
| 2018/0064364 A1 | 3/2018 | Oziel | |
| 2019/0021627 A1 | 1/2019 | Elliott | |
| 2021/0169413 A1 | 6/2021 | Wyeth et al. | |

FOREIGN PATENT DOCUMENTS

| | | |
|---|---|---|
| CN | 101052347 A | 10/2007 |
| CN | 102159129 A | 8/2011 |
| CN | 102238906 | 11/2011 |
| CN | 102481435 A | 5/2012 |
| CN | 203000923 U | 6/2013 |
| CN | 103442634 A | 12/2013 |
| CN | 103598883 A | 2/2014 |
| EP | 2111787 A1 | 10/2009 |
| GB | 2396421 | 6/2004 |
| JP | S56-27509 | 3/1981 |
| JP | S60-37905 | 3/1985 |
| JP | H01-212341 | 8/1989 |
| JP | 05-237073 | 9/1993 |
| JP | 2001-502832 | 2/2001 |
| JP | 2002-062323 | 2/2002 |
| JP | 2007-272413 | 10/2007 |
| JP | 2011-030106 | 2/2011 |
| JP | 2011-526191 | 10/2011 |
| JP | 2014-504936 A | 2/2014 |
| JP | 2014-519352 A | 8/2014 |
| JP | 2016-515404 A | 5/2016 |
| JP | 2016-515880 A | 6/2016 |
| WO | WO2000074572 | 12/2000 |
| WO | WO2006135520 | 12/2006 |
| WO | WO2007108914 | 9/2007 |
| WO | WO2009144461 | 12/2009 |
| WO | WO2009158601 | 12/2009 |
| WO | WO2010129026 | 11/2010 |
| WO | WO 2012140510 A2 | 10/2012 |
| WO | WO2013110001 | 7/2013 |
| WO | WO2013140744 | 9/2013 |

(56) References Cited

FOREIGN PATENT DOCUMENTS

| WO | WO2014152374 | 9/2014 |
|---|---|---|
| WO | WO2016036946 | 3/2016 |

OTHER PUBLICATIONS

Sun et al. "The detection of chronic cerebral hemorrhage in rabbits with magnetic induction." Journal of Physics: Conference Series. vol. 407. No 1 IOP Publishing, 2012. (10 pages).
Beehive Electronics Datasheet. 100 Series EMC Probes. Sebastopol, California. 4 pgs, Apr. 13, 2009.
Bey et al., "Second impact syndrome," West J Emerg Med., 10(1):6-10, Feb. 2009.
Boody et al., "Accuracy in the measurement of compartment pressures: a comparison of three commonly used devices," J Bone Joint Surg Am., 87(11):2415-2422, Nov. 2005.
Borchardt, "The Beginnings of Drug Therapy: Ancient Mesopotamian Medicine" (Abstract only), Drug News Perspect., 15(3):187-192, Apr. 2002.
European Search Report for Application No. 17163167.4, dated Jul. 10, 2017, 7 pages.
Gonzales et al., "In Vivo Inductive Phase Shift Measurements to Detect Intraperitoneal Fluid," IEEE Trans Biomed Eng., 54(5):953-956, May 2007.
Gonzales et al., "Over-hydration detection in brain by magnetic induction spectroscopy," Journal of Physics Conference Series, 224: 012123, 2010, 4 pages.
Gonzales et al., "The detection of brain ischaemia in rats by inductive phase shift spectroscopy," Physiol. Meas., 30 (8): 809-819, Epub Jun. 30, 2009.
Gonzales et al., "The detection of brain oedema with frequency-dependent phase shift electromagnetic induction," Physiol. Meas., 27(6): 539-552, Epub Apr. 7, 2006.
Gonzales et al., "Volumetric electromagnetic phase-shift spectroscopy of brain edema and hematoma," PLoS One, 8(5):e63223, May 14, 2013.
Griffiths et al., "Magnetic induction tomography. A measuring system for biological tissues," Ann N Y Acad Sci., 873:335-345, Apr. 20, 1999.
Len et al., "Cerebrovascular Reactivity Impairment After Sport-Induced Concussion", Official Journal of the American College of Sports Medicine, Clinical Sciences, Medicine & Science in Sports & Exercise by the American College of Sports Medicine, http://www.acsm-msse.org, pp. 2241-2248, 2011.
Roberts et al., "Mannitol For Acute Traumatic Brain Injury," The Cochrane Database of Systematic Reviews, Issue 2, Art No. CDOO 1049. DOI:10.1002/14651858. CD001049, The Cochrane Collaboration. Published by John Wiley & Sons, Ltd., Mar. 1, 2005, pp. 1-7.
Smith, "Signal and Noise Measurement Techniques Using Magnetic Field Probes," http://www.emcesd.com/pdf/emc99-w.pdf., IEEE 1999 EMC Symposium Proceedings, pp. 559-563, 1998.
Sun et al., "Silent brain injury after cardiac surgery: a review: cognitive dysfunction and magnetic resonance imaging diffusion-weighted imaging findings," J Am Coll Cardiol., 60(9):791-797, Aug. 28, 2012.
Ullman, "Wireless Helmet Detects Brain Trauma," Baylor Innovations, 8(1): 14-15, Jun. 2014.
Wise et al., "The value of hypertonic mannitol solution in decreasing brain mass and lowering cerebro-spinal-fluid pressure," J Neurosurg., 19:1038-1043, Dec. 1962.
Xu et al., "Study of PSSMI for Cerebral Hemorrhage Detection: An Experimental Simulation," 2011 4th International Congress on Image and Signal Processing (CISP), IEEE, pp. 266-268, Oct. 15, 2011.
European Search Report and Written Opinion Application No. 13738728.8, dated Aug. 25, 2015, 5 pages.
International Search Report & Written Opinion for PCT/US2013/022316 dated Apr. 30, 2013, 7 pages.
International Search Report & Written Opinion for PCT/US2015/048336, dated Dec. 8, 2015, 13 pages.
International Search Report & Written Opinon for PCT/US2016/069209, dated Jun. 26, 2017, 13 pages.
European Search Report for Application No. 16921385.7, dated Jun. 4, 2020, 7 pages.

HEADSET DEVICE FOR DETECTING FLUID IN CRANIUM VIA TIME VARYING MAGNETIC FIELD PHASE SHIFTS AND HARMONICS OF FUNDAMENTAL FREQUENCIES

CROSS-REFERENCE TO RELATED APPLICATIONS

This application is a continuation of U.S. patent application Ser. No. 14/690,985, entitled "Method for Detecting Fluid in Cranium Via Time Varying Magnetic Field Phase Shifts," filed Apr. 20, 2015, now U.S. Pat. No. 10,335,054, which is a continuation of U.S. patent application Ser. No. 14/275,549, entitled "Method for Detecting and Treating Variations in Fluid," filed May 12, 2014, which is a continuation of U.S. patent application Ser. No. 13/745,710, entitled "Diagnostic Method for Detection of Fluid Changes Using Shielded Transmission Lines as Transmitters or Receivers," filed Jan. 18, 2013, now U.S. Pat. No. 8,731,636, which claims priority to U.S. Provisional Patent Application Ser. No. 61/588,516, filed on Jan. 19, 2012, entitled "Diagnostic Device for Detection of Fluid Changes in the Brain and Other Areas of the Body," all of which are hereby incorporated by reference in their entireties.

TECHNICAL FIELD

This application is related to noninvasive, diagnostic, medical devices, systems and methods. More specifically, some embodiments of this disclosure relate to devices, systems and methods that use magnetic induction phase-shift spectroscopy ("MIPS") to monitor changes in fluids in the brain or other parts of the body.

BACKGROUND

In many different medical settings, it would be advantageous to be able to detect changes in bodily fluids as they occurred in a noninvasive manner. For example, it is often critical to monitor intracranial changes in fluid in an intensive care unit patient. Standard of care for these patients includes invasive monitors that require drilling a hole in the cranium and inserting a probe such as an intracranial pressure (ICP) monitor, or microdialysis or "licox" probes for measuring chemical changes to the fluids in the brain. No noninvasive measurement techniques are currently commercially available for detecting cerebral fluid changes such as would occur with bleeding or edema, and many brain injuries are not severe enough to warrant drilling a hole in the cranium for invasive monitoring. Thus, for many patients with brain injury, there is no continuous monitoring technology available to alert clinical staff when there is a potentially harmful increase in edema or bleeding. Instead, these patients are typically observed by nursing staff, employing a clinical neurological examination, and it is not until increased fluid in the brain causes observable brain function impairment that the physicians or nurses can react. In other words, there is no way currently available for monitoring intracranial fluid changes themselves, and thus the ability to compensate for such changes is limited.

MIPS has been previously proposed for diagnosis of brain fluid abnormalities. Patents have been awarded for proposed devices, and promising scientific studies of prototype devices are described in the literature. For example, Rubinsky et al. described the use of MIPS for this purpose in U.S. Pat. Nos. 7,638,341, 7,910,374 and 8,101,421, the disclosures of which are hereby incorporated in their entirety herein (referred to herein as the "Rubinsky Patents"). However, no practical, mass-produced medical device based MIPS technology has yet emerged to provide clinicians specializing in brain treatment or other areas of medicine the promised benefits of such a device.

It was first postulated by Albert Einstein that the velocity of the transit of electromagnetic radiation in a vacuum is equal to the inverse of the square root of the product of magnetic permeability and electric permittivity. This formula yields the well-known value of the speed of light of approximately $3 \times 10^8$ meters/second. The finite time required for an electromagnetic field to propagate through a medium, however, results in a time delay, which is manifested as a phase shift (e.g., an offset or a delay) between a field emitted from a transmitter as compared with the field as sensed at a receiver. In other words, electromagnetic fields typically propagate fastest in a vacuum, and propagate slower if any matter or medium is present between the transmitter and the receiver. The amount of slowing is inversely proportional to the square root of the product of the relative permeability and relative permittivity of the medium.

The material makeup of biological materials is almost entirely non-magnetic, with a relative permeability of approximately 1. The variation in the time delay/phase shift through biological materials may therefore be mainly dependent on the average relative permittivity along the path through which the electromagnetic field passes. Relative permittivity varies for various tissue types and body fluids. The permittivity of the biological materials may also depend on the frequency of a time-varying electromagnetic field and may depend on the ambient temperature. The relative permittivity of body fluids is higher than most brain tissues, and thus, changes in fluid levels in the brain may have a relatively large effect on the overall phase shift of electromagnetic fields as they propagate through a brain or other medium.

For radiofrequency ("RF") frequencies below about 200 MHz, the distance between opposing sides of the brain is less than one wavelength for normally propagating transverse electromagnetic waves. This is known as the near field, and in this region the electromagnetic waves are not fully formed. For this near field magnetic field propagation case, the propagation time and phase change is predominately determined by the loss factor of the tissues and liquids in the path rather than their relative permittivity. The loss factor is a function of the imaginary portion of the complex permittivity and the conductivity. The physical mechanism for dissipation of energy is the constant realignment of polarized molecules to the changing field polarity. Therefore the loss factor for a given substance is largely dependent on its ionic content. The ionic content of brain tissue and brain liquids is different for each substance. When combined with variations in relative permittivity, the various biological tissues and liquids in the brain display unique phase signatures when looking at phase changes for both the lower frequency near field propagation and higher frequency normal propagation cases. Because of the major difference in the physics that causes the phase delay, a multi-spectral measurement using RF frequencies both below and above 200 MHz allows characterization of not only the fractional amount of liquid in the brain, but sub-classifications of the exact nature of the liquid content such as the fractions of blood, cerebrospinal fluid (CSF), or the other liquids that accumulate in the cerebral cavity due to hemorrhaging or edema.

Again, despite research into use of MIPS for diagnosis of fluid changes in the body, no practical medical device based MIPS technology for doing so currently exists. A strong need exists for such technology. Ideally, a medical device solution would provide a MIPS system with improved performance, usability and manufacturability, such that it could be used for noninvasive fluid change detection in the brain and/or other areas of the body. At least some of these objectives will be addressed by the embodiments described herein.

SUMMARY

Generally, MIPS measurements of electromagnetic fields may be used to detect changes in fluid levels in an area of a body. Detected changes in fluid levels in various parts of the body may be used to monitor or assess disease states, and in some cases, detected fluid level changes may be used to determine or adjust a medical or surgical treatment to be administered to the patient. For example, abnormal fluid changes in the brain may be used to help determine treatment of abnormalities such as bleeding, edema, or ischemia due to stroke or brain trauma. In other areas of the body, detection of abnormal fluid level changes may be used to help treat conditions such as congestive heart failure, lymphedema, and many others.

The present disclosure provides methods and systems to improve the absolute accuracy of the phase shift measurements and also to the repeatability of phase shift measurements. The present disclosure also includes a more detailed description of the physics of the mechanism that produces the phase shift, as well as a correlation of phase shift changes to the biological processes taking place in brain-injured patients. Practical methods are also presented for converting the quantitative phase shift measurement data into a qualitative assessment of brain health.

Although phase shift is a good way to measure changes to the electrical properties of tissue that accompany fluid changes, various embodiments described herein may alternatively use other techniques to measure such changes. For example, magnitude changes may be used in some embodiments to measure changes to electrical properties of tissues. The magnitude of the received radiation at the RF detector is affected by the distance from the emitter, the geometry and orientation of the emitting and receiving antennae, and the type and geometry of the various materials in the path. At lower RF frequencies, the absorption of most biological materials is quite low. There is significantly more absorption, however, if electrical conductivity or electromagnetic field losses in the material is high. The shape and granularity of the materials in the radiation path can cause scattering or refractive lensing, which also strongly affects the magnitude of the detected radiation. The change in phase is a more significant effect than the attenuation of the magnitude, and is also easier to decipher. However, the magnitude data may be useful as a quality check to assure that the emitter and detector are properly aligned at the time of an individual phase measurement, or for other purposes. So, while this disclosure will focus primarily on phase shift measurements, various embodiments may alternatively or additionally employ other techniques.

The disclosure provides a means of measuring phase shift of time-varying electromagnetic fields after passing through a patient's brain using a non-invasive, non-contact method. The electromagnetic fields may be produced by a small transmitter placed on one side of the patient's head that converts a time-varying input current (for example, a sinusoidal-type signal) into a time-varying magnetic field. A small receiver or detector placed on the other side of the patient's head may detect the magnetic field, after passing through the patient's head, and convert the same to a received time-varying current, in one embodiment. Although the frequency of the received time-varying magnetic field will be the same as the frequency of the transmitted time-varying magnetic field, there will be a shift in the phase angle between the two fields, which is dependent on the frequency of the signals and the medium through which the magnetic field propagates from the transmitter to the receiver. In various embodiments, equivalent voltages may be used in place of currents to measure the magnetic field as transmitted and/or as received.

The current in the transmitter and the current in the receiver may be sampled by one or more analog to digital (A to D) converters at appropriate sampling rates and intervals determined by a sampling signal. The conversion from analog electrical signals to digital data may occur in some embodiments proximate the transmitter and/or receiver located near the patient's head. The acquired digital samples of the emitted and received magnetic fields may then be transmitted via digital signal busses back to a remote processing unit or processor or processing element for processing in some embodiments. In other embodiments, the analog electrical signals are passed from the transmitter and receiver through a coaxial cable to an A to D converter in a remote processing unit.

In one embodiment of a diagnostic system for monitoring changes in a medium described herein, the system includes a transmitter configured to generate and transmit a time-varying magnetic field into a medium responsive to a first signal. The system also includes a receiver positioned on an opposite side of the medium from the transmitter and configured to generate a second signal responsive to a received magnetic field at the receiver. The system also includes a processing unit configured to determine a phase shift between the transmitted magnetic field and the received magnetic field for a plurality of frequencies of the transmitted time-varying magnetic field. At least one of the transmitter or the receiver includes a loop formed using a shielded transmission line.

In some examples, the transmission line may include a first conductor as a shield that at least partially encloses a second conductor, and the second conductor provides a signal responsive to a varying magnetic field. The transmission line may include one of a coaxial cable, a twisted shielded pair of wires, a twinaxial cable, or a triaxial cable, and/or the first conductor may form a Faraday cage around the second conductor. The shielded transmission line may include a strip line on a printed circuit board coupled between two grounded planes in some examples, and there may be a plurality of vias between the two grounded planes. The loop may have a diameter of approximately one inch, may be a single turn loop, and/or may have a lowest natural resonant frequency above 200 MHz. In some examples, the loop may be a first loop positioned in a first layer of a printed circuit board, and the system may further include a second loop positioned in a second layer of the printed circuit board and formed using strip line, with leads from both the first and second loops are coupled to a differential amplifier. The printed circuit board may also include a plurality of grounded shielding planes positioned above and below the loop in the printed circuit board. The grounded shielding planes may each define a circular void, with an internal diameter of the circular void being smaller than an internal diameter of the loop. A balun may be coupled to the loop and configured to balance the output of the loop, and/or the output of the loop may be balanced to effectively have a 50 ohm output impedance.

Also, in some examples, the system may include a first analog to digital converter coupled to the transmitter and positioned proximate the transmitter, and also may include second analog to digital converter coupled to the receiver and positioned proximate the receiver. The first analog to digital converter and the transmitter may be coupled to a single printed circuit board. The processing unit may include a sampling signal generator configured to generate a sampling signal, the sampling signal having a frequency to under-sample the transmitted and received magnetic fields. The processing unit may further be configured to average a plurality of respective samples of the transmitted and received magnetic fields and determine the phase shift between the averaged transmitted magnetic fields and the averaged received magnetic fields. The processing unit may include a sampling signal generator configured to generate a sampling signal, with the sampling signal being such so as to coherently sample the transmitted and received magnetic fields. The processing unit may further be configured to calculate a fast Fourier transform of samples of the transmitted and received magnetic fields, and determine the phase shift by comparing the phase components of the calculated respective fast Fourier transforms.

In some examples, the transmitter may be a first transmitter and the time-varying magnetic field may be a first time-varying magnetic field, and the system may further include a second transmitter also configured to generate and transmit a second time-varying magnetic field into the medium responsive to a third signal, the second transmitter being offset from the first transmitter. A first frequency of the first time-varying magnetic field generated and transmitted by the first transmitter may be different from a second frequency of the second time-varying magnetic field generated and transmitted by the second transmitter. In some examples, the receiver may be a first receiver, and the system may further include a second receiver configured to generate a third signal responsive to a received magnetic field at the second receiver, the second receiver being offset from the first receiver. The processing unit may be configured to triangulate the location of a change in fluid responsive to the received magnetic field at the first and second receivers.

In some examples, the processing unit may be configured to reduce errors in the determined phase shift resulting from movement of the transmitter, the receiver, or a patient. The system may include an accelerometer coupled to the transmitter or to the receiver, and the processing unit may exclude data corresponding to periods of time wherein the accelerometer detects significant motion of the transmitter or receiver. The processing unit may exclude data corresponding to periods of time during which the determined phase shift between the transmitted magnetic field and the received magnetic field is such that it is unlikely the result of biological changes within the medium. The processing unit may further be configured to initialize the diagnostic system responsive to an air scan.

In some examples, the receiver may be a first receiver, and the system may further include a second receiver positioned proximate the transmitter and configured to generate a third signal responsive to the transmitted magnetic field and indicative of the phase of the magnetic field proximate the transmitter. The second receiver may be concentric within the first receiver.

In some examples the processing unit may include a first FPGA configured to synthesize the first signal, a second FPGA configured to collect and average a first plurality of samples from the second signal and a second plurality of samples representative of the phase of the transmitted magnetic field, a third FPGA configured to determine a phase measurement based on the averaged first and second plurality of samples, and a microcontroller coupled to the first, second, and third FPGAs and configured to control the first, second, and third FPGAs.

In another embodiment of a diagnostic system for monitoring fluid changes in a patient described herein, the system may include a headset and a transmitter coupled with the headset and configured to generate and transmit a time-varying magnetic field into the patient responsive to a first signal. A receiver is also coupled with the headset such that it is located on approximately an opposite side of the patient's head from the transmitter when the headset is applied to the patient's head and configured to generate a second signal responsive to a received magnetic field at the receiver. At least one spacer is disposed between the transmitter and the patient's head and the receiver and the patient's, and a processing unit is configured to determine a phase shift between the transmitted magnetic field and the received magnetic field for a plurality of frequencies of the transmitted time-varying magnetic field.

In some examples, the headset may include an elastic headband, and the system may also include stabilizers that couple the transmitter and receiver to the patient's head. The stabilizers may be moldable to the patient's head to hold the transmitter and receiver in place, and the spacers may be plastic disks.

In another embodiment of a method for monitoring intracranial fluid in a patient described herein, the method includes transmitting a first time-varying magnetic field from a transmitter toward a receiver, wherein the transmitter and the receiver are coupled to approximately opposite sides of the patient's head via a headset, and wherein at least one spacer is disposed between each of the transmitter and the patient's head and the receiver and the patient's head. The method also includes receiving the first magnetic field with the receiver, and determining a baseline phase shift between the transmitted magnetic field and the received magnetic field for a plurality of frequencies of the transmitted time-varying magnetic field. The method also includes transmitting, at some time after the first time-varying magnetic field is transmitted, a second time-varying magnetic field from the transmitter toward the receiver, receiving the second magnetic field with the receiver, and determining a new phase shift between the transmitted magnetic field and the received magnetic field for a plurality of frequencies of the transmitted time-varying magnetic field. The method also includes comparing, with a processor coupled with the headset, the new phase shift to the baseline phase shift, determining, using the processor and based on the comparison between the new and baseline phase shifts, whether a clinically significant change in intracranial fluid has occurred, and generating a signal, via the processor, if it is determined that the clinically significant change has occurred.

In some examples, the method may also include converting the received magnetic fields with an analog to digital converter coupled directly with the headset at or near the receiver, and may also include converting the transmitted magnetic fields with an analog to digital converter coupled directly with the headset at or near the transmitter. Generating the signal may include triggering an alarm.

In some examples, the first and second magnetic fields are in a frequency range of about 20 MHz to about 300 MHz.

Also, the method may include, before transmitting the first time-varying magnetic field, initiating the headset by transmitting a calibration magnetic field from the transmitter to the receiver while the headset is not coupled with the patient. At least one of the transmitter or the receiver may include a loop formed using strip line on a printed circuit board, wherein the loop has a diameter of approximately one inch and is a single turn loop.

In some examples, the method may further include detecting motion of the patient with a motion detection member, transmitting a signal to the processor based on the detected motion, and distinguishing, using the processor, the comparison of the new and baseline phase shifts from the detected motion of the patient.

In some examples, the method may further include calculating, with the processor, a fast Fourier transform of samples of the transmitted and received magnetic fields, and determining the first and second phase shifts by comparing phase components of the calculated respective fast Fourier transforms. In some examples, coupling the headset with the patient's head may include positioning an elastic headband on the head, wherein the transmitter and the receiver are mounted to the elastic headband, and wherein a spacer is coupled with each of the transmitter and receiver so as to be disposed between the transmitter and receiver and the patient's head when the headband is positioned on the head.

In some examples, the steps of the method may be repeated multiple times over time to monitor the fluid over time. The method may also include recommending a treatment, based on the generation of the signal, and the treatment may be an amount of mannitol to be delivered to the patient to reduce an amount of intracranial fluid.

DETAILED DESCRIPTION

Certain details are set forth below to provide a sufficient understanding of certain embodiments of the present disclosure. However, some embodiments of the disclosure may be practiced without these particular details. Moreover, the particular embodiments of the present disclosure are provided by way of example and should not be used to limit the scope of this disclosure to those particular embodiments. In some instances, well-known circuits, control signals, timing protocols, and software operations have not been shown in detail in order to avoid unnecessarily complicating the description.

Overall System Architecture

Figure 1:
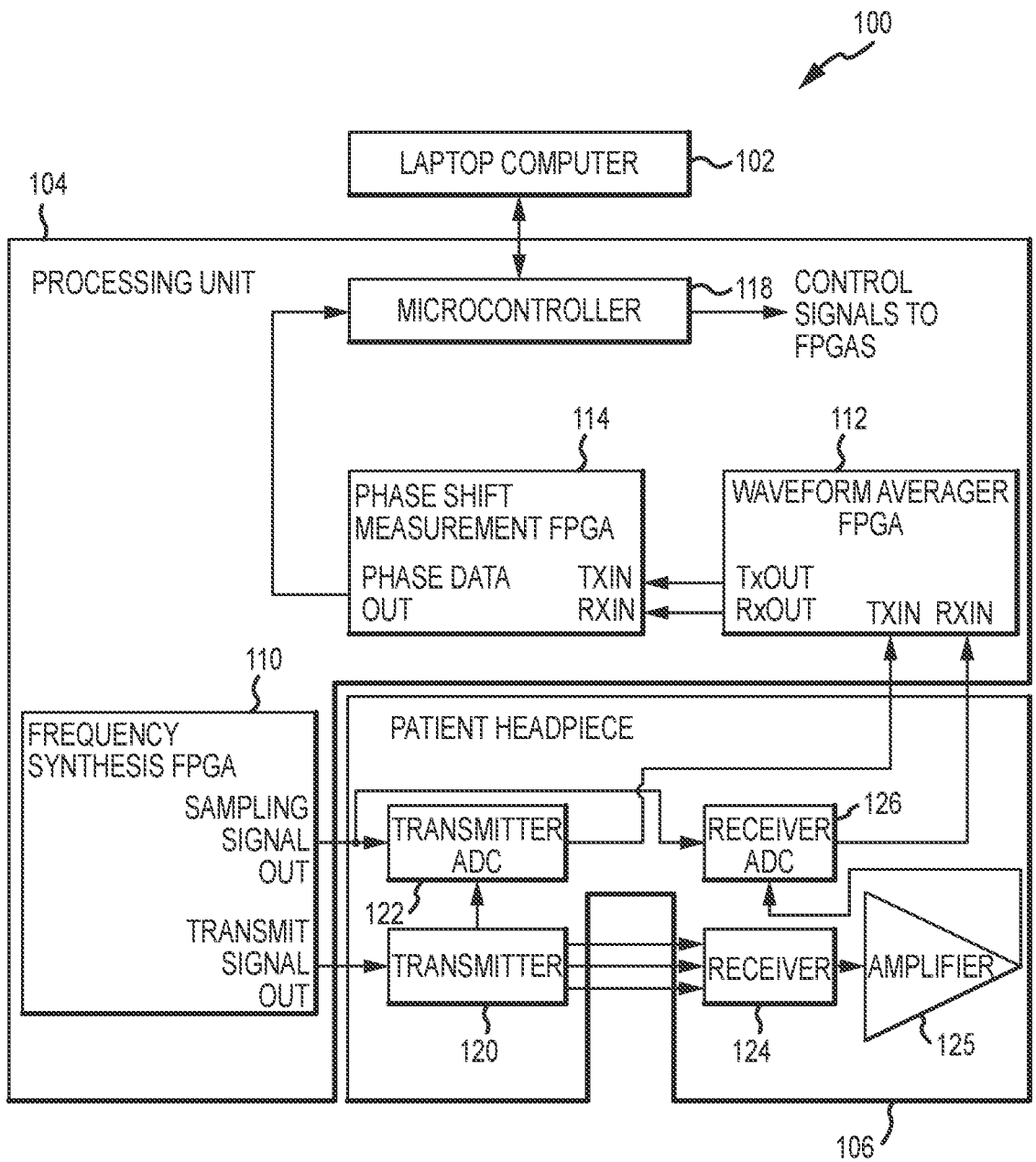
FIG. 1 is a block diagram of a system for monitoring fluid changes in the body, according to one embodiment.

FIG. 1 is a block diagram of one embodiment of a system 100 that may be used to detect fluid changes in a human brain. Although this description often focuses on use of the system 100 for detecting fluid changes in the brain, this embodiment of the system 100 or alternative embodiments may be used for detecting/monitoring fluid changes in any other part of the body. Therefore, the exemplary description provided herein that is directed toward the brain should not be interpreted as limiting the scope of the invention as it is set forth in the claims.

The system 100 may include a laptop computer 102, a processing unit 104, and a patient headpiece 106 in some examples. The system 100 may be controlled, for example, by a Windows-based LabView language program running on the laptop computer 102. The program generates a graphical user interface (GUI) that is displayed on the screen of the laptop 102. The clinician who operates the system 100 may initiate monitoring by mouse control after placing the headpiece 106 on the patient, which may be similar to an elastic headband or bandage. After initiation of monitoring, the program may run unattended as it logs the phase shift data on the laptop 102 and applies the appropriate methods to generate alarms and suggested corrective actions to a clinician.

The laptop 102 may have a USB serial link to the processing unit 104. This USB link may be electrically isolated to conform to applicable medical device requirements. The processing unit 104 may derive power from a standard universal AC line power connection consistent with international standards. There may be a medical grade low-voltage DC power supply to power all of the processing unit's 104 internal electronics that meets applicable standards for patient isolation, line to neutral, chassis, and patient leakage as well as earth to ground continuity, EMI susceptibility and emissions, and other standard medical device requirements.

The laptop 102 may initiate phase shift data collection and log the data in files on the laptop's 102 hard drive along with other pertinent data and status information.

The GUI on the laptop 102 may control the operation of the system 100, and may include controls and status indications that guide the clinician through installation of the patient headpiece 106 and a preliminary self-test of the entire system 100. If the self-test passes, the clinician is instructed to initiate monitoring. During monitoring, the phase shift angle versus frequency data is collected from the USB interface and appropriate status and alert methods are applied to the data. The clinician may be informed if additional actions or emergency responses are indicated. The phase shift versus frequency data and additional status information is logged in the laptop 102 for later reference. A "sanity check" of the data and other built-in-test features may run continuously in the background, and if a fault is encountered, various levels of severity will generate warnings or interrupt operation of the system 100.

The architecture of hardware and firmware in the processing unit 104 and the patient headpiece 106 may be optimized to achieve the desired phase measurement accuracy and stability while using a minimum number of custom electronics components in some examples and as illustrated in FIG. 1. For example, in one embodiment, and with reference to FIG. 1, the system 100 may comprise several highly integrated miniaturized off-the-shelf components.

The system 100 may include three field programmable gate arrays (FPGAs) 110, 112, 114 in the processing unit 104, the three FPGAs being programmed with appropriate firmware. One FPGA 110 may synthesize a time-varying signal to be provided to a transmitter 120 to generate a magnetic field, the second FPGA 112 may collect and average digital samples of transmitted and received magnetic fields, and the third FPGA 114 may measure the phase shift between the transmitted and received signals representative of the transmitted and received magnetic fields.

A microcontroller 118 may also be included in the processing unit 104, and may supervise the actions of the three FPGAs 110, 112, 114 and communicate with the laptop 102 (e.g., by transferring phase data results). The microcontroller 118 may provide an interface between the external laptop computer 102 (via an electrically isolated USB interface) and the FPGAs 110, 112, 114 used for real time signal processing of the data from the headpiece 106. The microcontroller 118 may also perform other miscellaneous functions such as the interface to basic user controls including power-on, initiation of data collection, setup of the frequency synthesizer 110, internal temperature monitoring, power supply monitoring, and other system status monitoring and fault detection tasks.

The processing unit 104 may in some examples be fabricated from larger, integrated components. In one embodiment, the processing unit 104 may include an off-the-shelf electronic signal generator, such as a Techtronix Arbitrary Waveform Generator model 3252, and a digital oscilloscope such as LeCroy Model 44xi.

The architecture of the system 100 illustrated in FIG. 1 may be relatively flexible, allowing improvements in all phases of the data collection, data processing, and data interpretation (e.g., clinical alerts) to be made through relatively simple software or firmware modifications. The FPGAs 110, 112, 114 may effectively function as parallel processors to make data collection and processing proceed in near real time. The quantity of phase data transmitted via the microcontroller 118 to the laptop 102 and archived for later reference may thus be reduced, thereby requiring less computation time on the laptop 102 for processing the data. This may in turn free up the laptop 102 for checking data consistency and applying methods required for alerting clinicians to the need for corrective actions.

Although the processing unit 104 in FIG. 1 has been illustrated and described as a relatively flexible embodiment, in other examples the diagnostic system 100 may be an embedded system with custom electronics components specially designed for use in the diagnostic system 100. For example, one or more A to D converters may be located in the processing unit 104, which may be physically distinct and separate from the headpiece 106, or which may be integral with the headpiece 106 (e.g., the headpiece 106 may, in a custom system 100, include all of the electronics and processing equipment needed to capture and process phase shift information). In general, any suitable architecture may be used.

Referring again back to FIG. 1, the system 100 may also include a headpiece 106 with one or more transmitters 120 and one or more receivers 124, the details of which are explained in more detail below. In one example, the headpiece 106 includes a single transmitter 120 and a single receiver 124, whereas in other examples, the headpiece 106 includes several transmitters 120 and/or several receivers 124. For example, the headpiece 106 may include one transmitter 120 and two receivers 124. If multiple receivers 124 are placed at different positions over a patient's head, they may allow a clinician to triangulate the location of a fluid change (e.g., intracerebral bleeding from a blood vessel or tumor) and/or image the biological impedance of a patient's brain. In other examples, the headpiece 106 may include multiple transmitters 120, which may produce magnetic fields at different or similar frequencies. If different frequencies are used, a single or multiple receivers 124 may be able to distinguish among the several transmitted frequencies in order to, for example, further distinguish the type of fluid change.

In some examples, in addition to the receiver 124 positioned elsewhere on the patient's head, an additional receiver may be positioned on the same side of the patient's head as the transmitter 120 (e.g., the receiver may be concentric within or may circumscribe the transmitter 120, or may be positioned in a separate plane from the transmitter 120) in order to obtain a measurement of the transmitted magnetic field from the transmitter (not shown in FIG. 1). In other examples, the emitted magnetic field may be sampled from the transmitter 120 in another fashion, such as by measuring the current and/or voltage present on the transmitter 120. In some examples, and with reference to FIG. 1, the patient headpiece 106 includes A to D converters 122, 126 for one or more of the transmitter(s) 120 and/or receiver(s) 124 proximate the respective transmitter(s) 120 and/or receiver(s) 124 themselves—for example, A to D converters may be positioned on the same printed circuit board as the respective transmitters 120 or receivers 124 in some examples.

In other examples, however, the analog signals are not converted into digital signals until after being passed through one or more coaxial cables (or other transmission lines) connected to a separate processing unit (e.g., the processing unit 104 shown in FIG. 1). In these examples, various techniques may be employed to reduce cross-coupling between, for example, a coaxial cable carrying a signal indicative of the transmitted magnetic field from the transmitter 120 and a coaxial cable carrying a signal indicative of the measured magnetic field from the receiver 124. For example, a relatively flexible RF-316 double shielded cable may be used to increase the isolation between the two cables, or, in other examples, triple shielded cables may be used. As another option, highly flexible PVC or silicone tubing may be provided around the coaxial cable from the receiver 124 and/or transmitter 120.

Figure 1A:
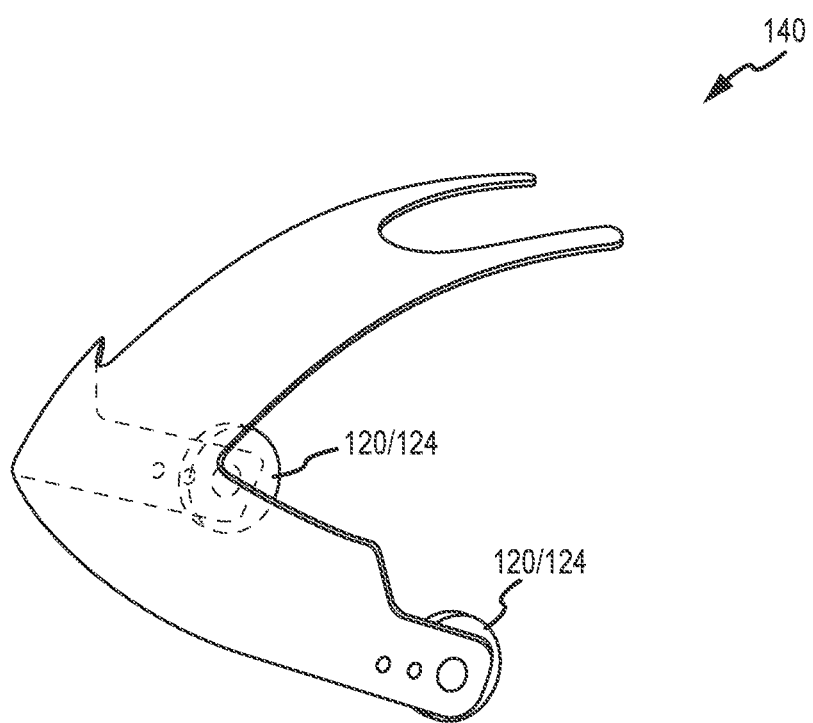
FIG. 1A is a perspective view of a patient headpiece for use in the system of FIG. 1, according to one embodiment.

Referring again to the headpiece 106 illustrated in FIG. 1, for repeatable readings, it may be important for the transmitter 120 and receiver 124 to not move during operation of the system 100 because such movement may introduce an error in the phase shift measurement. In order to overcome such errors, the transmitter 120 and receiver 124 may be mounted in a rigid manner in some examples, for example in an apparatus that resembles a helmet 140, one example of which is illustrated as FIG. 1A. The helmet 140 may provide the necessary support and rigidity to ensure that the transmitter 120 and receiver 124 remain fixed relative to each other and relative to the patient's head. However, such a helmet 140 may be uncomfortable or impractical to use on a patient while they are lying down. Also, it may not be practical for a patient to wear the helmet 140 for several days as may be desirable in some clinical situations.

Figure 1B:
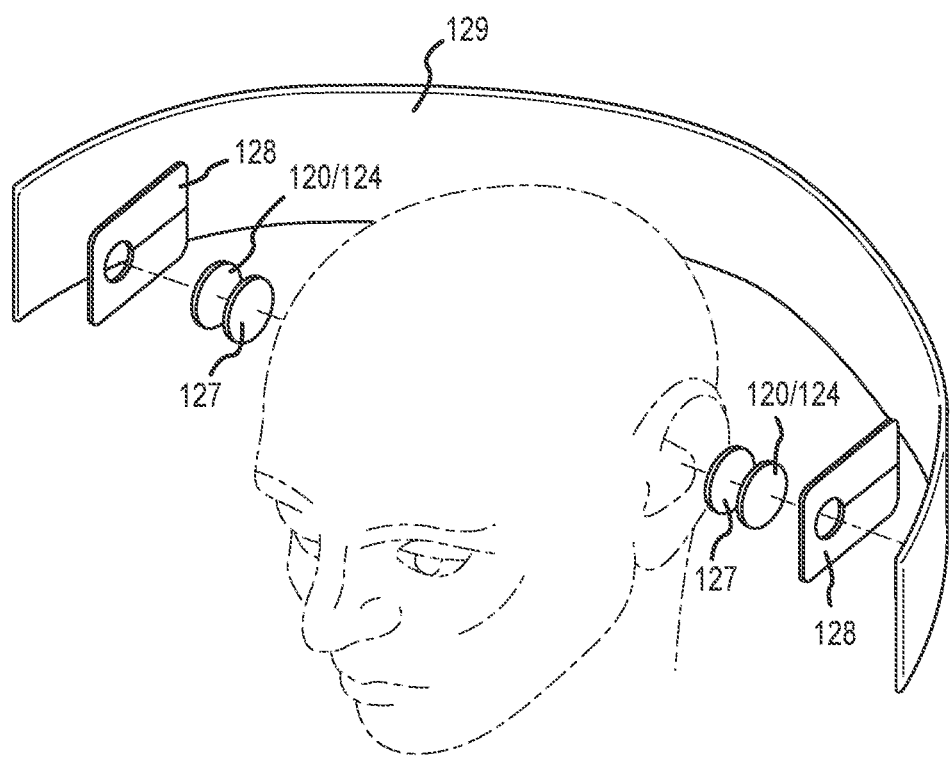
FIG. 1B is a perspective exploded view of another patient headpiece for use in the system of FIG. 1, according to one embodiment.

Accordingly, in an alternate embodiment, and with reference to FIG. 1B, the transmitter 120 and receiver 124 are held against the head of the patient using a headset 129, such as an elastic band 129. The transmitter 120 and receiver 124 may be mounted on the headset 129, for example, by securing them inside a pocket of the headset 129, or using stitches, rivets or other fasteners. The transmitter 120 and receiver 124 may be spaced at a fixed distance from the surface of the skin by incorporating a non-conductive spacer material 127, such as plastic or fabric. The spacers 127 can serve the purpose of maintaining a fixed distance between the transmitter 120 and receiver 124 from the skin in order to, for example, reduce variability of the capacitance between the transmitter 120/receiver 124 and the skin. The spacers 127 may be, for example plastic acrylic disks in some embodiments. Rubber, medical adhesive, or other material may also or alternatively be used for the spacers 127, and may be placed at the skin interface surface of the transmitter 120 and receiver 124 to aid in keeping them from moving during use. The headset 129 may be placed on the patient's head across the forehead and around the back of the head in some embodiments; or a different band or other device can be placed in other configurations, including around a patient's arm or leg. In other words, any suitable positioning device may be used to appropriately position the transmitter 120 and receiver 124 proximate the area of the patient's body under investigation, of which the headsets 106, 129 and headbands 129 described herein are merely examples. Additional features such as a chin strap or a connection over the top of the head can be added to the headset 129 to provide additional stability and to provide features on which to mount additional transmitters 120 or receivers 124. Since the patient will often be lying on a pillow, a convenient location for electrical components and for cable terminations might be the top of the head. For example, a bridge from a point near each ear may be created so that the electronics can be mounted at the top of the head, away from the surfaces that the patient may lie on. Low-profile components that are lightweight may be used so as to maximize comfort and minimize the tendency of the headset to move on the patient's head once in place.

In the headset 129 design, a headband 129 may be made of elastic, rubber, acrylic, latex or other flexible material, and may be elastic or inelastic. The headset 129 may be fabricated from inexpensive materials so the headset can be a disposable component of the system. Alternatively, the headset 129 may be reusable. If it is reusable, the band 129 may be washable so that it can be cleaned between patients, or cleaned periodically for the same patient. Washable materials may include plastic, rubber, silicone, fabric, or other materials. The headpiece 106 may also include mounting means for securing the electronic components and to route the cables to keep them from getting in the way of the patient or the clinical staff.

In some embodiments, including those where a headband 129 is used, in order to reduce the relative motion between the transmitter 120/receiver 124 and the patient, one or more stabilizers 128 may be used. Stabilizers 128 may be custom-molded to the patient's body to hold the transmitter 120 and/or receiver 124 in place. As one example of a stabilizer 128, trained clinicians may install the transmitter 120/receiver 124 using low-melting-point plastic that is similar to orthopedic casts made from the same material. Other custom-shapeable materials and methods may be used, such as materials which polymerize over time, or with activation by heat or chemical reaction such as materials used for making orthopedic casts or splints.

With reference now to the exploded view of FIG. 1B, the operation of one embodiment of using a headset 129 will be described, although it will be understood that similar bands 129 may be used to monitor fluid change in other parts of the body, such as a bandage wrapped around a leg or an arm. Each transmitter 120/receiver 124 may first be coupled to a respective spacer 127 by, for example, a screw or other fastener such as glue. The transmitter 120 and respective spacer 127 may then be positioned on a patient's head, and the stabilizer 128 may be positioned around the transmitter 120/spacer 127 in order to stabilize the transmitter and help prevent movement. The stabilizer 128 may need to be soaked in water or otherwise prepared for application prior to positioning it around the transmitter 120/spacer 127. Once the stabilizer 128 secures the transmitter 120/spacer 127, another stabilizer 128 may similarly be used to stabilize the receiver 124 and spacer 127 in a similar manner. The stabilizers 128 may solidify or dry out to perform the stabilizing function. Then, a headset such as a headband 129 may be wrapped around the stabilizers 128 and transmitter 120/spacer 127 and the receiver 124/spacer 127. In some embodiments, however, no stabilizers may be used, and the headband 129 may instead be used to directly position the receiver 124/spacer 127 and the transmitter 120/spacer 128 on the patient's head. In still other embodiments, and as mentioned above, the headband 129 may include pockets for the transmitter 120 and receiver 124, with the headband 129 material itself acting as a spacer. Also, in some embodiments, the headband 129 may have non-slip material applied to an interior side of the headband 129 to help prevent slippage of the headband 129 on the patient's head.

The apparatus and methods described herein may be used, in various embodiments, for fluid measurement (often fluid change measurement) in all parts of the body and for multiple medical diagnostic applications. The configuration of the emitter and detector coils may be modified, in various embodiments, to be appropriate to the area of the body and/or the diagnostic application involved. For example, for an application involving a limb, such as the arm, or where it may be more important to measure liquid content at a shallow depth in the tissue, the emitter coil and detector coil may be placed on the same side of the subject tissue. A co-planar arrangement may be appropriate. Since the coils may be separated by a much shorter distance, the received signal strength may be much greater, and the size of the coils may be reduced. In various alternative embodiments, the coils may be in a side-by-side co-planar arrangement or in a concentric co-planar arrangement using coils with different diameters. In some embodiments, it may be more appropriate to place the plane of the coils at a slight angle to conform to the shape of the body part under study.

Figure 6:
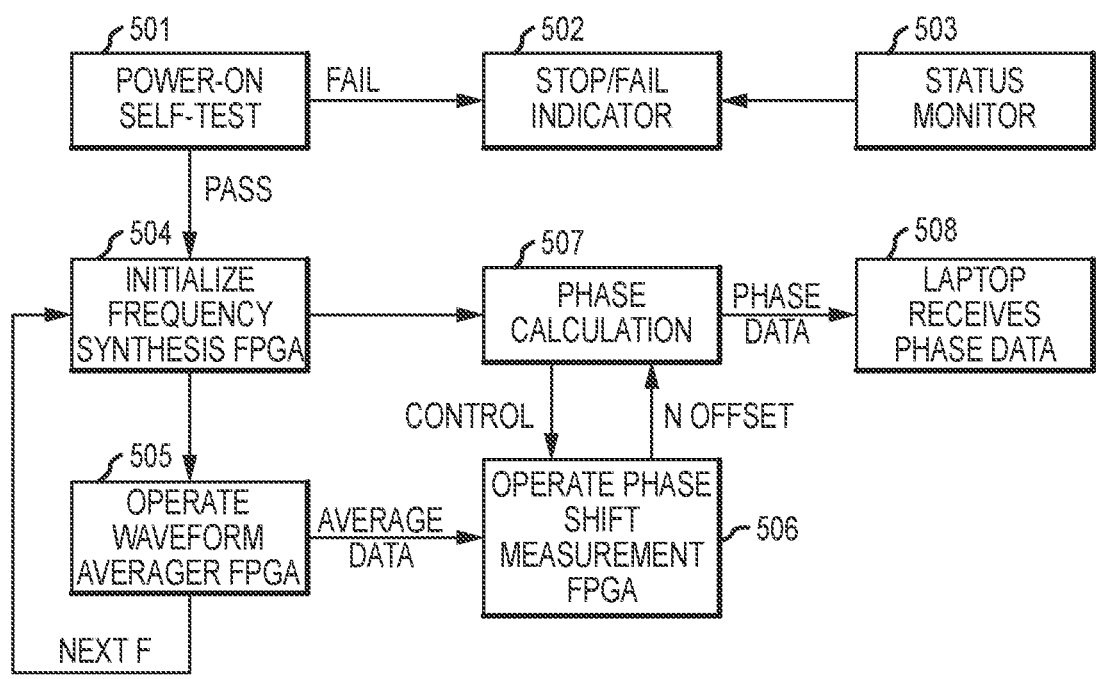
FIG. 6 is a flow diagram for the operation of the system of FIG. 1, according to one embodiment.

With reference now to FIG. 6, one example of the operation of the system 100 will now be briefly described, it being understood that various operations illustrated in FIG. 6 will be described in more detail below, and various alternative methods and modes of operation will also be described below. Beginning at operation 501, the system 100 is powered on and a self-test is performed. If the system 100 fails the test, a stop or fail indicator is displayed on the laptop 102 in operation 502. If the system 100 passes the power-on self-test, operation moves to operation 504. Also, throughout operation of the system 100, a continuous status monitor may run in operation 503, and, should the status monitor determine that system 100 is failing, the system may display a stop or fail indicator in operation 502.

Once the system 100 passes the power-on self-test and operation has moved to operation 504, the frequency synthesis FPGA 110 may be initialized and begin to provide the transmitter 120 with the transmit signal in operation 504. The waveform averager FPGA 112 may begin to collect and average waveforms from the transmitter 120 and the receiver 124 in operation 505. The averaged waveforms may be provided to the phase shift measurement FPGA 114, which may determine the phase shift between the transmitter 120 and receiver 124 waveforms beginning in operation 506, with the ultimate phase calculation of interest being calculated in operation 507. The phase calculation may be provided to the laptop 102 in operation 508. At any point after operation 505, the frequency synthesizer FPGA 110 may provide another frequency to the transmitter 120, and the process may repeat for the next frequency. Multiple frequencies may thus be emitted from the transmitter 120 and subsequent phase shifts calculated. For example, the frequency synthesis FPGA 110 may provide the next frequency in repeated operation 504 while the phase shift measurement FPGA 114 measures the phase shift between the waveforms from the previous frequency, or the frequency synthesis FPGA may not provide the second frequency until the phase calculation has been provided to the laptop in operation 508. In an alternate embodiment, the emitter can emit a single frequency simultaneously with harmonic frequencies, or through the use of multiple frequency generators, for later separation using techniques such as Fast Fourier Transform (FFT). Simultaneous emission of multiple frequencies can be advantageous for noise cancellation, motion rejection and other purposes.

The Transmitter(s) and Receiver(s)

One range of electromagnetic frequencies appropriate for an inductive phase shift measurement based system 100 for brain fluid diagnostics is in the radio frequency (RF) range from about 20 MHz to 300 MHz, although other frequencies may also be used, such as between 1 MHz and 500 MHz, between 3 MHz and 300 MHz, and so forth. The frequencies chosen may provide relatively low absorption rates in human tissues, good signal relative to noise factors, such as capacitive coupling and signal line cross-talk, and ease of making accurate phase measurements.

Previously, certain examples of transmitters (and corresponding receivers) that emit (and sense) magnetic fields in these frequency ranges were constructed of thin inductive coils of a few circular turns placed such that the plane of the coil is parallel to the circumference of the head. (See, for example, the Rubinsky Patents, previously incorporated herein by reference.) The coils of these previous transmitters and receivers had diameters of 10 cm or more and 5 or more turns. These relatively large transmitter and receiver coils, however, were cumbersome and furthermore had resonances within the range of the frequencies of interest for MIPS detection of fluid in a human brain. When transmitter or receiver coils are operating in a frequency near one of their natural resonant frequencies, a measured phase shift may be largely a function of the magnitude of the coil's own parasitic capacitances, and very small changes due to motion of either of the coils and/or environmental effects can cause large changes in the phase shift, creating unacceptable noise in the measurement of phase shift.

Accordingly, in some embodiments of the present disclosure, the lowest natural resonant frequency of the transmitter 120 and/or receiver 124 may be higher than the intended frequencies of the magnetic fields to be transmitted. In some examples, the transmitter 120 may include a coil as a magnetic field generator or transducer. From symmetry considerations, this same or a similar coil may act as a magnetic field sensor in a receiver 124. In either case, as the diameter of the coil and number of turns (i.e., loops) is reduced the first self-resonant frequency generally increases. The limit, therefore, is for a coil with a single loop, the loop having a very small diameter. As the loop diameter decreases, however, the amount of magnetic flux intercepted by the loop is reduced by a factor equal to the ratio of diameters squared. Likewise, the induced voltage in the loop is reduced, resulting in a smaller signal from a loop acting as a magnetic field sensor in a receiver 124. Thus, there are practical limits on the diameter reduction. In some embodiments, however, an additional increase in the self-resonant frequency can be achieved by using transmission line techniques in the construction of the transmitter 120/receiver 124.

An alternative to using coils designed for a relatively constant phase shift over a wide bandwidth is to add external reactive components in a series-parallel network to tune out the phase shift at a single frequency or at a small number of discrete frequencies. This concept works best if the approximate value of the individual frequencies is known prior to designing the overall system and the number of discrete frequencies is small. By using switched or motor driven tunable components, the phase shift tuning can be automated and software controlled. An advantage of tuning to a constant phase shift is that it provides more freedom in the choice of the size and shape of the coils. Using larger coils can increase the detected signal strength and provide a field shape that is optimally matched to the portion of the brain or other body part that is being sampled.

Figure 2A:
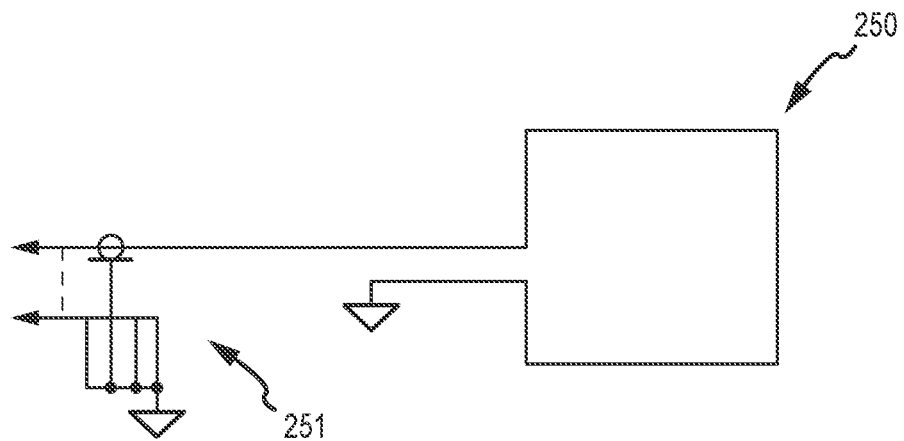
FIGS. 2A through 2F illustrate various embodiments of transmitter transducers and receiver sensors for use in the system of FIG. 1.

In one embodiment, with reference to FIG. 2A, a single loop 250 with a high self-resonant frequency and associated stable phase response below the self-resonant frequency may be constructed using a shielded transmission line, such as coaxial cable, buried strip-line on a printed circuit board, a twisted shielded pair of wires, a twinaxial cable, or a triaxial cable. The loop 250 may be used as either a magnetic field generator in the transmitter 120 or as a magnetic field sensor in the receiver 124. The shielded transmission line may include a first conductor as a shield 251 that at least partially encloses a second conductor. The first conductor or shield 251 may be grounded and may form a Faraday cage around the second conductor. The second conductor may provide an output signal responsive to the changing magnetic field, and, due to the Faraday cage, the second conductor may be shielded from external electrostatic effects and from capacitive coupling. For example, in one embodiment, a single loop 250 of buried strip line may be sandwiched between two grounded planes in a printed circuit board. A plurality of vias may extend between the two grounded planes, with the spacing of the vias determined by the wavelengths of the electromagnetic field being transmitted and/or received, and the vias together with the two grounded planes forming an effective electrostatic or Faraday cage around the buried strip line loop 250. In other embodiments, other types of transmission lines with an outer shield (such as coaxial cable) may be used in order to form a Faraday cage and thus reduce external electrostatic effects on the loop 250.

Figure 2B:
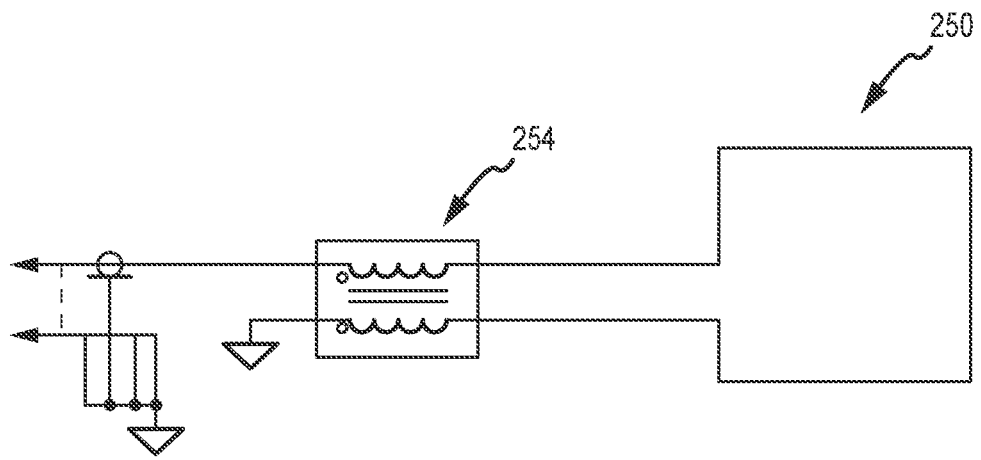
Figure 2C:
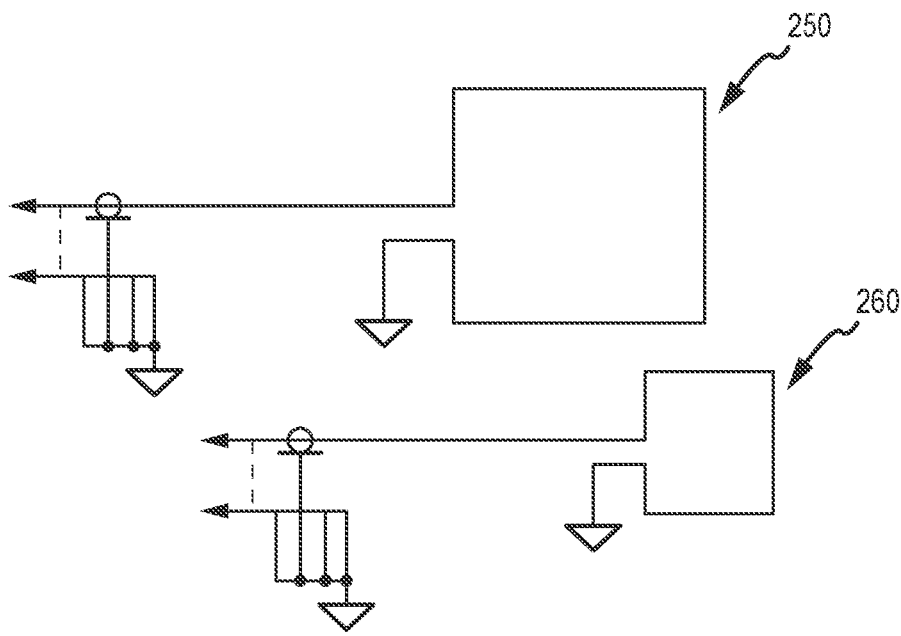
Figure 2D:
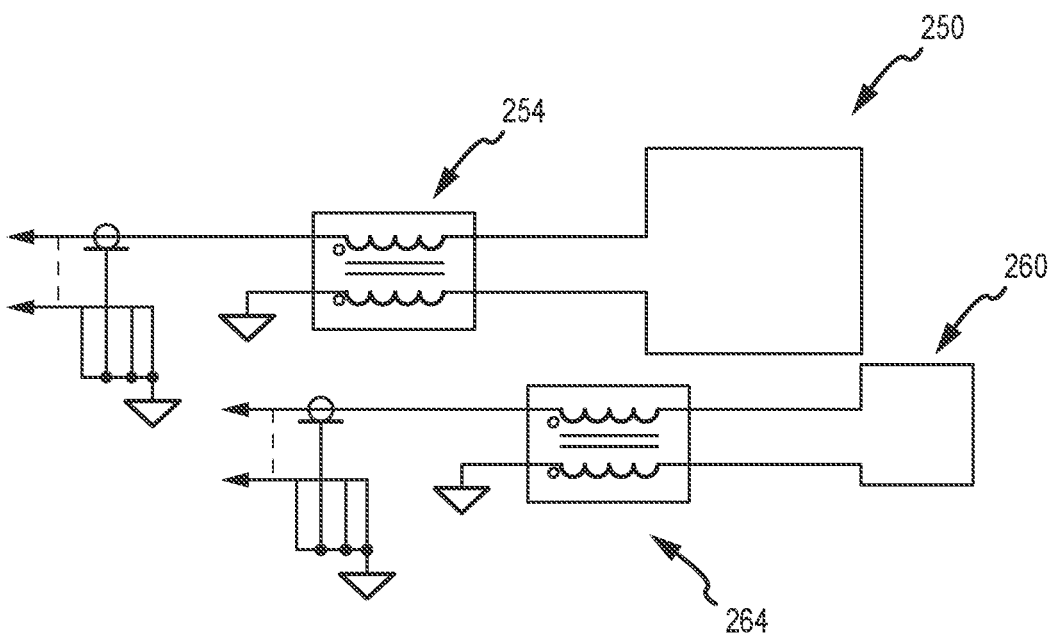

In single loop 250 embodiments of a transmitter 120 or receiver 124, the voltage of the loop 250 may not be in phase with the current of the loop 250 due to the inductive nature of the single loop 250. This phase error may be detected and accounted for during initialization of the diagnostic system 100, as described below. In some embodiments of the single transmitter loop 250, however, and with Reference to FIG. 2B, a balun transformer 254 may be added, in order to obviate the need to correct for this phase error. In still other embodiments, and with reference to FIG. 2C, a second, independent, smaller, concentric loop 260 is used to sense the transmitted magnetic field and provide a current representative of the same to the A to D converter. The second, concentric transmitter loop 260 may in some examples be the same size as the corresponding receiver loop (e.g., in receiver 124) in order to have proportional signals and good uniformity between them, whereas in other examples the receiver loop may be larger than the second, concentric transmitter loop 260 in order to be more sensitive to the received magnetic field. In those transmitters 120 with the second, concentric transmitter loop 260, and with reference to FIG. 2D, a balun transformer 264 may likewise be used on this second, concentric loop 260 in order to balance the sensed voltage and current. Furthermore, for a single-turn receiver loop 250, a balun 254 may likewise be added in order to also balance its performance, similar to that shown for the transmitter cable in FIG. 2B.

Figure 2E:
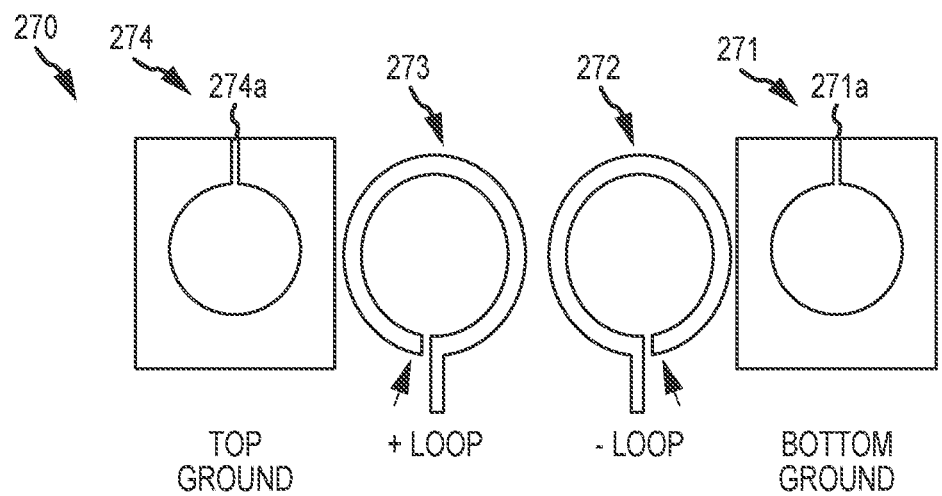

Referring now to FIG. 2E, in another embodiment, the transmission line concept may be extended from building a single-loop, single-ended device to building a dual-loop 270, which may be double-ended or "balanced," for use as a receiver 124 (or, symmetrically, for use as a balanced transmitter 120). In FIG. 2E, four conductive (e.g., copper) layers 271, 272, 273, 274 may be formed on a printed circuit board as shown, with three layers of dielectric material (not shown in FIG. 2E) coupled between the four conductive layers 271, 272, 273, 274 when stacked vertically. The top and bottom layers 271, 274 may be grounded and thus form an electric shield. Furthermore, small linear breaks 271a, 274a may be present in both of the top and bottom layers 271, 274 so that the ground planes 271, 274 don't act like additional shorted turns. In between the top and bottom ground layers 271, 274, the +loop 273 and the −loop 272 may be positioned, with the leads from the two loops 272, 273 being coupled to a balanced amplifier (not shown in FIG. 2E). The +loop 273 and the −loop 272 may be center tapped in some examples. The inner diameter of the two loops 272, 273 may be approximately 1 inch, and may be slightly greater than the inner diameter of the circular void in the two grounded planes 271, 274. In some embodiments, the thickness and permittivity of the dielectric material, the width and thickness of the conductive material forming the loops 272, 273, the spacing of the ground planes 271, 274, and so forth, may be chosen such that the double loop 270 has approximately a 50 ohm impedance in order to match the transmission line to which it will be coupled. In this manner, the self-resonant frequency of the dual loop structure 270 may be above 200 MHz in some examples.

Still with reference to FIG. 2E, for a dual loop 270 used as a magnetic field sensor in a receiver 124, external noise that is coupled into the system 100 from environmental changes in the magnetic field due to environmental EMI sources or motion of nearby conductors or magnetic materials may be reduced due to the common-mode rejection of the differential amplifier to which the two loops 272, 273 are coupled. Having the differential amplifier coupled to the loops 272, 273 when used as a receiver 124 thus may allow the loops' 272, 273 diameters to be reduced while keeping the output signal level at a suitable level for transmission to a remote processing unit 104 (e.g., for those systems where one or more A to D converters are not located directly in the headpiece 106). The amplifier power gain may be approximately 40db in some embodiments. Low-cost wide-bandwidth amplifiers offering gains of 40db for the power levels of interest are readily available in miniaturized packages from multiple suppliers with negligible phase shift variation over a 20 MHz to 200 MHz frequency range.

Figure 2F:
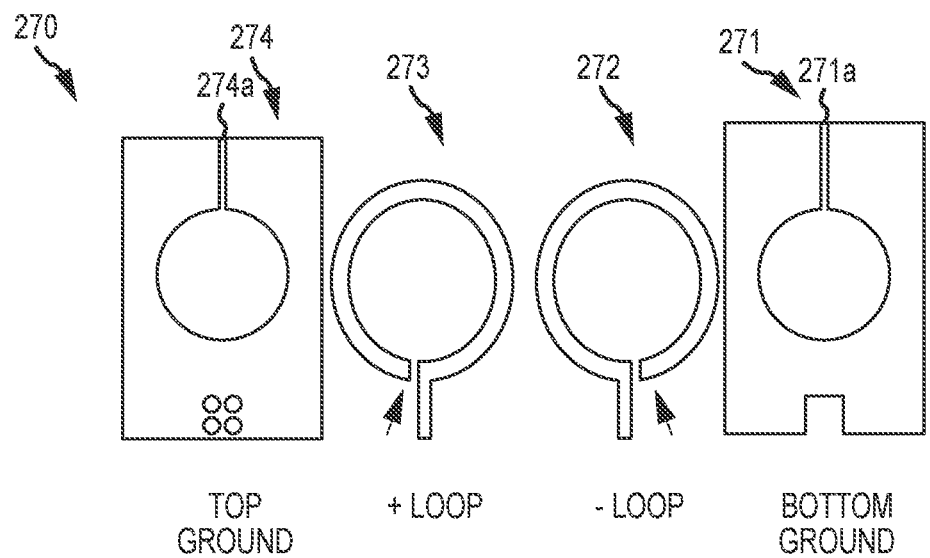

With reference to FIG. 2F, as suggested, the dual loop 270 used for a balanced receiver 124 has an analogous application as a magnetic field generating transmitter 120. The balanced approach for constructing a transmitter 120 may result in a common-mode cancellation of noise in the transmitted magnetic field due to the opposite winding directions of the dual loops, thus reducing noise in the transmitted magnetic field that may otherwise result from electrostatic or magnetic pickup from environmental factors.

Referring still to FIGS. 2E and 2F, in some embodiments, the two loops 272, 273 may be formed in different planes, or, in other embodiments, the two loops may be fabricated in the same plane with concentric circular strip-line traces (thus reducing the number of layers required in fabricating the PC board). This concentric design may be used for the transmitter 120, and/or the receiver 124.

Also, with reference to any of FIGS. 2A through 2F, in examples where the analog to digital conversion is not done proximate the transmitter 120 or receiver 124, a resistive attenuator may be added to the PC board with surface-mount resistors in order to help reduce cross-coupling of the transmitter signal to the receiver signal in the cable through which the analog signals are transmitted, which may help increase phase measurement accuracy and stability. The on-board attenuator may result in a substantial size and cost reduction compared with a bulky separate modular attenuator. Also, still continuing with examples where the analog to digital conversion is not done proximate the transmitter 120 or receiver 124, with reference still to any of FIGS. 2A through 2F, one or more amplifiers may be provided to amplify the signals from the transmitter 120 and/or the receiver 124 in order to reduce attenuation of the signals through the cable to the external analog to digital converter 122, 126. Still continuing with examples where the analog to digital conversion is not done proximate the transmitter 120 or receiver 124, the voltage on the transmitters and receivers may be in phase with current on the respective transmitters and receivers because the "balanced" transmitter and receivers illustrated in FIGS. 2E and 2F are terminated in the 50 ohm characteristic impedance of coaxial line.

Figure 3:
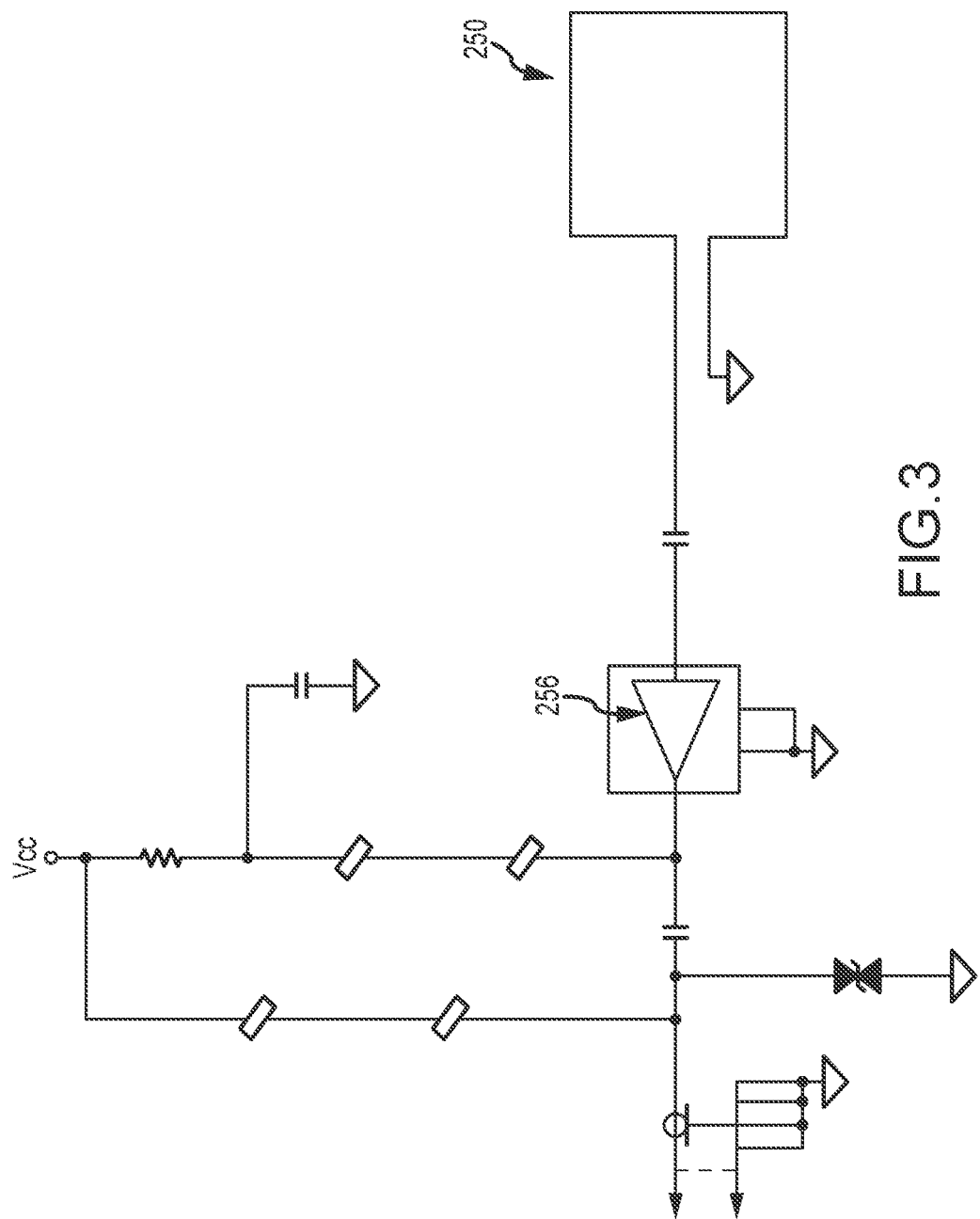
FIG. 3 is a circuit diagram of a phase shift detection apparatus, according to one embodiment.

Referring now to FIG. 3, an alternative design may include an amplifier 256 on the same printed circuit board as the loop 250. Including an amplifier 256 on the same printed circuit board as the loop 250 (that is used, for example, as a receiver 124) may help increase the signal to noise ratio, which may be particularly useful for embodiments where analog to digital conversion is done remotely from the headpiece 106. An amplifier 256 may also be used in embodiments where analog to digital conversion of a signal is done near the loop 250. As mentioned above, a balun transformer (not shown in FIG. 3) may be also included on the printed circuit board between loop 250 and the amplifier 256, which may help cause the coil to operate in a "balanced" mode. In the balanced mode, capacitively coupled electromagnetic interference pickup or motion induced fluctuations in the signal level may be reduced or canceled, since they typically equally couple into both the negative and positive leads of the balanced differential signal.

Initialization: Air-Scan to Remove Fixed-Phase Errors

As suggested above, the diagnostic system 100 may be initialized in some examples in order to calibrate the transmitter 120 individually, the receiver 124 individually, the transmitter 120 and the receiver 124 with one another and with the other associated electronics, and so forth. For example, variations in lead lengths and amplifier time delays in signal paths from the transmitter 120 and receiver 124 may be detected during initialization and removed from the signals during signal processing in order to prevent fixed offset errors in the data. Also, any phase shift between (measured) voltages and currents in a single-turn loop 250 may be detected.

The initialization may in one embodiment be an "air-scan" where the transmitter(s) 120 and receiver(s) 124 are positioned with only air between them, the transmitter(s) 120 and receiver(s) 124 positioned approximately as far apart as they would be if they were positioned on the head of an average patient. Once thus spaced, phase shift data is collected for a range of different frequencies (because the errors may be constant across or varying among different frequencies), and the collected air-scan values may be subsequently used during signal processing to correct any phase shift errors of the system 100 (e.g., by subtracting them from the values obtained during operation of the system 100). The initialization may be done when the A to D converters 122, 126 are in the headpiece 106 proximate to the transmitter 120 and receiver 124, when the A to D converters 122, 126 are external to the headpiece 106, and so forth.

Generation of the Driving and Sampling Signals

As mentioned above, the diagnostic system 100 collects phase shift data for transmitted time-varying magnetic fields at multiple frequencies because the phase shifts contributed by various tissue types and body fluids may vary with frequency. The diagnostic system 100 illustrated in FIG. 1 provides a flexible frequency synthesizer 110 within the processing unit 104, although in other embodiments, a frequency synthesizer 110 may be provided in, for example, the headpiece 106. This frequency synthesizer 110 may have a minimum of 1 MHz resolution over the range of about 20 MHz to 200 MHz in some examples (or alternatively about 20 MHz to 300 MHz or about 10 MHz to 300 MHz or any of a number of other suitable ranges). Standard digital phase-lock loop techniques may be used to derive the selectable frequencies from a single stable crystal-controlled clock oscillator. As described above, the digital portions of the synthesizer 110 may be implemented in one of the FPGAs 110 in the processing unit 104. The synthesizer 110 may produce both a basic square wave clock signal for generating the magnetic field in the transmitter 120 as well a sampling signal. The sampling signal may be at a slight offset (e.g. 10 KHz) in frequency from the magnetic field generating signal in some embodiments. The square wave signal for generating the magnetic field may, in some embodiments, be amplified to correct its level and may also be filtered to eliminate higher order harmonics and achieve a low distortion sine wave at one or more fundamental frequencies.

In other cases, where frequency domain techniques such as FFT processing of the time domain data are used to calculate phase, it may be advantageous to accentuate the harmonics of the fundamental frequency. For these embodiments, additional circuits may be added after the basic frequency synthesizer to make the rise-time or fall-time of a square-wave or pulse wave-shape much faster, thereby increasing the relative amplitude and number of higher order harmonics. As mentioned previously, this embodiment allows generation of a "comb" of frequencies with a single burst of RF and the processing of the captured time domain data from the emitter and detector using Fourier techniques yields a simultaneous time correlated phase difference data set for each frequency in the "comb". This simultaneous capture of phase data from multiple frequencies may yield significant advantages for separating the desired information about the patient's brain fluids from motion artifacts or other effects that would affect an individual scan of the frequency where the phase data for each frequency is measured at different times. Sampling each frequency at different times in this case introduces noise that may be difficult to detect or remove.

As the signal used to generate the magnetic field is typically periodic, it may not be necessary to use a sampling frequency that is many times greater than the frequency of that signal to capture the phase information from a single cycle of the waveform, and instead an under-sampling technique may be employed in some examples. Under-sampling is similar to heterodyning techniques used in modern radios where a large portion of amplifier gain and the audio or video signal demodulation is performed in much lower intermediate frequency stages of the electronics (IF). Under-sampling, in effect, allows a system to collect the same or a similar number of sample points over a longer period of time, while not disturbing the phase information of the signal.

Using under-sampling may eliminate the need for high-speed A to D converters (which are expensive and may involve many different wired connections) that may otherwise be required to capture enough phase samples from a single cycle of the waveform to accurately measure phase angle. If a lower speed A to D converter may be used, it may be commercially and physically practicable to position the A to D converter 122, 126 proximate the transmitter 120 and receiver 124 loops 250, 270, as described above.

Therefore, in some embodiments, one or both of the transmitted and received magnetic field signals may be under-sampled (e.g., with one sample or less for each cycle) and an average record of the waveform may thus be captured using samples taken over a much longer interval of time compared to one cycle. In order to accomplish the under-sampling, both the transmit signal and the sampling signal may be derived from a common clock signal, with the sampling signal being accurately offset from the transmit signal frequency (or a sub-harmonic frequency) by a small amount. If the offset is, for example, 10 KHz from the first harmonic frequency of the transmit signal, the result after a period of 100 microseconds will be an effective picture of one cycle of the repetitive transmit waveform with f/10000 individual samples. For a transmit signal frequency of 100 MHz and sample frequency 100.010 MHz, the 10,000 under-sampled individual samples of a single cycle of the transmit waveform are spaced at a resolution of 360/10000 or 0.036 degrees. As one alternative to under-sampling, frequency conversion using standard non-linear mixing technology before an A to D converter 122, 126 may also be employed.

In other examples, the frequency of the magnetic field generator signal and the frequency of the sampling signal may be otherwise related, one example of which is described below when referring to frequency domain signal processing techniques. In still other examples, the sampling frequency may be relatively constant (e.g., 210 MHz, while the generating frequency may vary over a wide range).

Conversion of the Transmitted and Received Analog Signals to Digital Data

In some embodiments, electronic phase shift measurements between the transmit and receive signals may be performed using analog signal processing techniques, whereas in other examples the phase shift measurements may be performed after converting the analog data to digital data through one or more A to D converters 122, 126, as described above. The digital waveforms may then be processed to obtain the relevant phase shift information. Processing digital data rather than analog data may facilitate sampling and averaging many cycles of the waveforms in order to, for example, reduce the effects of random noise and, with proper techniques, even reduce non-random periodic noise such as AC line pickup at frequencies near 60 Hz. Also, after reducing the noise in the waveform data there are many methods, such as correlation, that may be employed to obtain accurate phase measurement using digital signal processing.

In some examples of the diagnostic system 100 described herein, the A to D conversion of both the transmitted and the received signals is performed as close as feasible to the point of generation and/or detection of the magnetic fields. For example, the A to D conversion may performed in the headpiece 106 by miniaturized monolithic single chip A to D converters 122, 126 located integral to the printed circuits that, respectively, contain the transmitter 120 and receiver 124. The A to D converter 122 for the transmitter 120, for example, may differentially sample the voltage across the balanced outputs of the transmitter 120 in one example. The A to D converter 126 for the receiver 124, for example, may be positioned at the output of a wide bandwidth signal amplifier coupled to the receiver 124. By locating the A to D converters 122, 126 on the headpiece 106 rather than in a remote processing unit 104 (which may, however, be done in other embodiments described herein) it may be possible to reduce or eliminate the effects of phase shifts associated with motion, bending, or environmental changes on the cables carrying the analog signals to the A to D converters 122, 126. Other sources of error that may be reduced or eliminated include cable length related standing-wave resonances due to small impedance mismatches at the terminations and cross-coupling between the transmit and receive signals on the interconnecting cables that generate phase errors due to waveform distortion. To realize similar advantages in an embodiment where the A to D converters 122, 126 are not located proximate the transmitter 120 and receiver 124, a single cable may be used to bring the sampling signal to the transmitter and receiver A to D converters 122, 126 in the processing unit 104, and/or a high quality semi-rigid cable may be used between the two A to D converters 122, 126 in some embodiments.

Overall Operation and Pipelining

Referring again to FIG. 1, the waveform data (which may be under-sampled in some embodiments) may be captured for both the transmitted and received magnetic fields, and the captured waveforms may be at least partially processed in real-time (or substantially real-time). As described herein, one FPGA 112 may average the data for each of the two waveforms over many cycles for noise reduction. Another FPGA 114 may then use a correlation technique to perform a phase shift measurement using the averaged waveform data. A pipelining technique may be used in some embodiments to speed up the data throughput for collection of phase data over multiple frequency samples. The transmitter 120 may generate a time-varying magnetic field at a first desired frequency, and the requisite number of waveform averages may be performed by the waveform averager FPGA 112 at this first frequency.

After the averager FPGA 112 collects and averages all of the sample data points from the transmitter 120 and receiver 124, it may transfer the same to the phase shift measurement FPGA 114. In some embodiments, only a single transmit frequency is used in diagnosing a fluid change in a patient, but in other embodiments, a plurality of different transmit frequencies within a desired spectral range may be generated and the corresponding data collected. In those embodiments with multiple transmit frequencies, phase determination for a first transmit frequency may proceed in the phase shift measurement FPGA 114 (using the data acquired during the first transmit frequency) while the frequency synthesizer FPGA 110 causes the transmitter 120 to generate a magnetic field having a second desired frequency of the spectral scan and the waveform data from the second transmit frequency is averaged by the waveform averager FPGA 112 (hence the pipelining). In other embodiments, the waveform averaging for one transmit frequency may occur substantially simultaneously with recording a plurality of samples for a second frequency. In general, many different types of pipelining (e.g., performing two or more parts of the signal generation, acquisition, and data processing at substantially the same time) may be used. In other embodiments, however, there may not be any pipelining, and the diagnostic system 100 may transmit, collect, average, and process all of the data relating to a single transmit frequency before moving to a second transmit frequency.

Regardless of whether pipelining is used, the process of using different transmit frequencies may be repeated for any number of transmit frequencies with a desired spectral frequency scan, and may also be repeated for one or more frequencies within the spectral scan. The calculated phase shifts for each frequency may be transferred to the laptop 102 directly from the phase shift measurement FPGA 114 in some examples.

Signal Processing—Averaging

Because of the relatively small size of the transmitter 120 and the receiver 124, as well as the relatively low power of the transmitted magnetic field (it is low power because of, among other things, the need to protect a patient from overexposure to RF radiation and the need to minimize electromagnetic field emissions from the system 100), the measured magnetic field at the transmitter 120 and/or at the receiver 124 may have relatively large amounts of noise compared to its relatively small amplitude. The noise may include input thermal noise of an amplifier, background noise from EMI pickup, and so forth. In some embodiments, the noise may contribute a significant fraction to the phase shift measurements relative to the actual phase shift. For example, 1 ml of fluid change may correspond with a 0.3 degree phase shift, and thus if the noise in the transmit and receive signals is a substantial portion of, or even exceeds, the expected phase shift, the noise may render the data unacceptable.

In order to reduce the noise, the diagnostic system 100 described herein may, in some embodiments, sample many cycles of the transmitted and received magnetic fields (e.g., many multiples of 10,000 samples, such as 32,000 samples) and may average the individual samples in order to substantially reduce random noise. In some examples, the total sampling time interval may be extended to be an approximate integer multiple of one 60 Hz AC power period in order to reduce the effect of 60 Hz related electromagnetic interference pickup. As explained below, these waveforms may be averaged by any appropriate averaging technique, including multiplying them by one another in the time domain, as well as other frequency domain averaging techniques.

Figure 4:
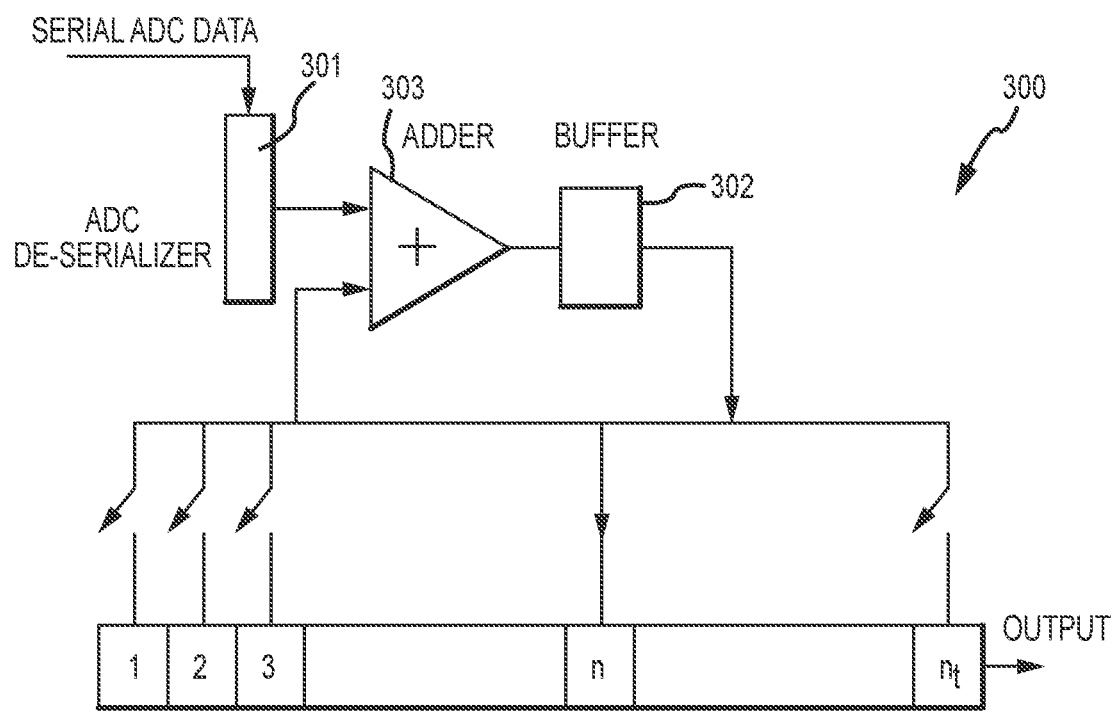
FIG. 4 is a simplified logic diagram for a waveform averager processor for use in the system of FIG. 1, according to one embodiment.

Referring now to FIG. 4, one embodiment 300 of a simplified logic diagram of the waveform averager FPGA 112 is shown. Of course, in other embodiments, custom circuitry may be employed to average data, which custom circuitry may be located in headpiece 106, in processing unit 104, in laptop 102, or in another suitable location. FIG. 4, however, illustrates one example of logic that may be implemented in the waveform averager FPGA 112 for averaging the transmitted waveform samples after they have been digitized by an A to D converter. Similar logic 300 may be used to average the received waveform samples after they have been digitized. The input to the waveform averager FPGA 112 may be a Low Voltage Differential Signaling (LVDS) type of format from the A to D converter, in order to reduce the wiring needed between an A to D converter and the waveform averager FPGA 112. In the LVDS format, each word of digital data representing a single waveform data-point may first be converted from serial data to parallel data by the deserialization logic described below.

The logic illustrated in FIG. 4 includes a synchronous serial-in, parallel-out shift register 301 that is clocked by the data transfer clock from the A to D converter. The parallel data words are then transferred into a memory buffer 302 with sufficient capacity to handle the maximum number of individual waveform samples required to construct one complete cycle of the transmitted waveform. An adder 303 may be used to accumulate the sum of all of the waveform samples in the memory buffer 302 as the data words exit the register 301 or after the memory buffer 302 is fully populated. Each waveform sum memory location may have a word size in bits that can accommodate the largest number expected for the sum without overflow. For example, a 12 bit resolution A to D converter and 4096 waveform sum requires a 24-bit memory word size. After accumulating the sum of the intended number of waveforms in the waveform memory for the transmitted signal samples (and, separately, the receiver signal samples are similarly summed in a waveform averager), the memory contents for both waveforms are serially transferred to the phase shift measurement FPGA 114. It may not be necessary to divide by the number of waveforms being averaged in some examples because, in the next step of the processing, only the relative magnitudes of the data-points in the averaged waveforms may be relevant. Because of this, an appropriate number of least significant bits may also be deleted from each of the averaged waveform data points without significant impact to the accuracy of the overall phase shift determination.

Signal Processing—Determining Phase Shift

Figure 5:
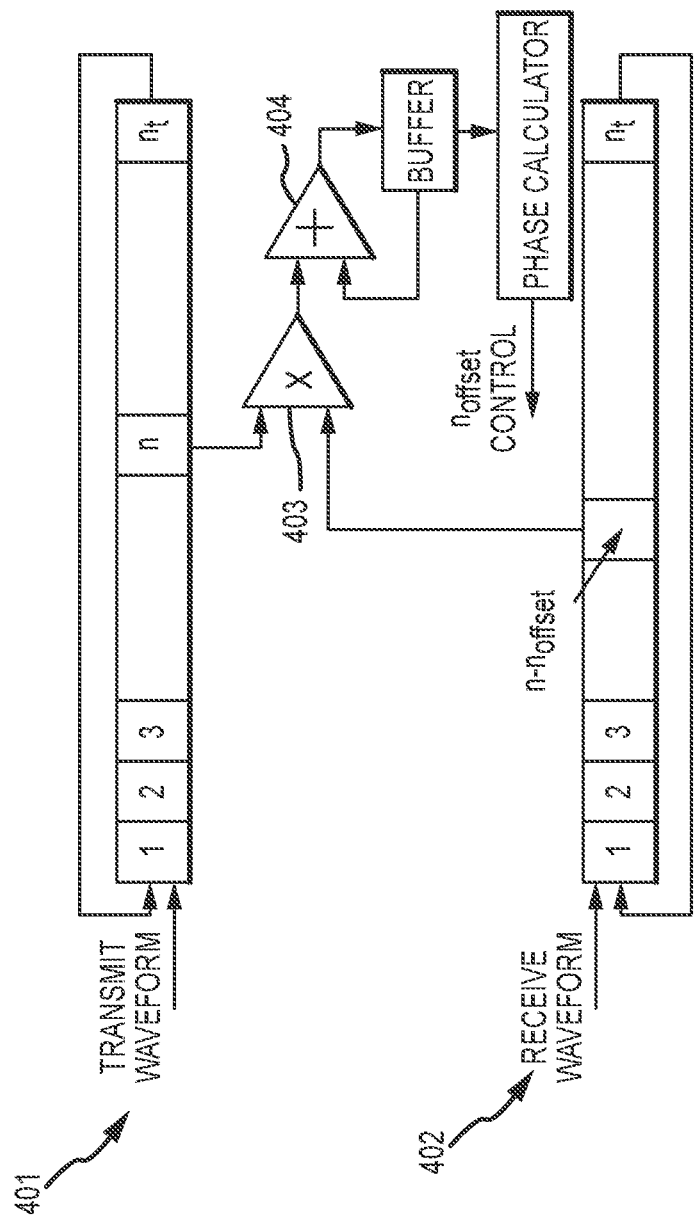
FIG. 5 is a simplified logic diagram of a phase shift measurement processor for use in the system of FIG. 1, according to one embodiment.

Referring now to FIG. 5, the phase shift measurement FPGA 114 may also contain two revolving shift registers 401, 402, a multiplier 403, and an adder 404. It may also include logic configured to calculate the sum of the product of the individual transmit and receive averaged waveform data points with an adjustable phase shift between the two waveforms. The FPGA may be used to find the phase shift where the sum of products is closest to zero and the slope of the sum of products versus phase shift is also negative.

Consider the following trigonometric identity for the product of two sine waves with frequency f and phase shift $\phi$:

$$\sin u \sin v = 1/2[\cos(u - v) - \cos(u + v)] \quad \text{(Eq. 1)}$$

where $$u = 2\pi f t + \Phi \text{ and } v = 2\pi f t$$

$$= 1/2[\cos(\Phi) - \cos(2\pi(2f)t + (\Phi))] \quad \text{(Eq. 2)}$$

The first term of the product is a DC term dependent only on the phase shift. The second term is another sine wave at twice the frequency which averages to zero over one complete cycle of the original frequency. Note that the first term (a cosine wave) is also zero when the phase angle ($\phi$) is either +90° or −90°. Furthermore the slope of the product with respect to phase angle change $d(\sin u \sin v)/d\phi$ is negative for $\phi=+90°$ and positive at $\phi=-90°$.

By iteration, the FPGA may determine the value of noffset where the transmitted wave and received wave are closest to a +90° phase shift. For an offset of noffset samples, and nt samples for one complete 360° waveform, the phase shift is then calculated using the following equation:

$$\text{Phase shift} = 90° + (\text{noffset}/nt)*360° \quad \text{(Eq. 3)}$$

The resolution of the determination may be limited to the number of samples (resolution=360°/nt). If this resolution is insufficient for the needed precision of the measurement, then interpolation may be used to find the fractional value of noffset where the sum of product terms exactly passes through zero.

Frequency Domain Signal Processing Methods for Phase Shift Measurement

As explained above (see e.g., sections on averaging and multiplying waveforms together to obtain phase shift data), the signal processing of the measured and digitized magnetic field traces from both the transmitter 120 and the receiver 124 may proceed in the time domain. In other embodiments, however, the signals may be processed in the frequency domain using, for example, fast Fourier transforms (FFTs)

In one embodiment of Fourier domain analysis, the signals from the transmitter 120 and receiver 124 are digitized at, for example, about a 200 MHz sampling rate with a relatively high resolution (e.g., 14 bits). The A to D converter and the data capture electronics may be included in a relatively small printed circuit assembly packaging. The captured data may be transferred via a high-speed USB serial link to the laptop computer 102. Time domain processing can then be replaced by frequency-domain processing on the laptop 102 to calculate the phase shift between the waveforms.

Once the data is on the laptop 102, the FFT for each of the transmitter and receiver time domain waveforms can be calculated (in other embodiments, however, the FFT may be calculated by an FPGA or other processor proximate the A to D converters). The resulting real and imaginary solutions which represent the resistive and reactive frequency domain data can then be converted from Cartesian to polar coordinates, thus yielding frequency domain plots of the magnitude and phase of the waveforms. The phase of each waveform can be obtained from the frequency domain plots of phase for the frequency of interest. If the fundamental frequency is off-scale, then a difference frequency between the sampling frequency and the transmitted wavefield frequency can be used. For example, a sample frequency of 210 MHz yields an FFT with a frequency range of 0 to 105 MHz, and the fundamental frequency is used for phase shift measurement when the transmitted wavefield frequency lies in this range. The difference frequency is used if the transmitted wavefield frequency is in the higher end of the range, for example, 105 MHz to 315 MHz.

After the FFT for both of the transmitted and received wavefield signals is calculated, the phase shift for a particular frequency of interest can then be calculated from the difference of the phase values obtained from the transformed transmitter and receiver waveforms. Note that some sign reversals for the phase information in various frequency regions may be needed when calculating the shift.

In order to allow FFTs to be computed for samples from the transmitter 120 and the receiver 124, the frequencies used for the sampling and the transmitted waveform may be determined so as to allow coherent sampling so that both the transmitted and received waveforms contain an integer number of complete time periods of the repeated waveform, and the number of samples collected for the waveforms is an even power of two. One method for implementing coherent sampling is to choose transmitter and receiver sampling frequencies such that prime1/ftransmit=prime2/freceive. The prime numbers prime1 and prime2, as well as the number of samples, can be very large in some embodiments, thereby reducing the spacing between the allowable values for the signal frequencies (e.g., the tuning resolution may be approximately 1 Hz). This may be accomplished by using digital frequency synthesis techniques, such as by combining a stable frequency source and the appropriate combinations of integer frequency multipliers, integer frequency dividers, and phase lock loops.

With coherent sampling, the theoretical accuracy of the phase calculation may only be limited by the number of samples of the time domain waveform and the digital resolution of the A to D converter. DC noise and low frequency noise sources such as 1/f noise may be inherently rejected by the frequency domain processing technique. The use of coherent sampling also reduces the probability that harmonic and intermodulation product frequency components will lie on top of the frequencies of interest for calculating phase. Furthermore, using an FFT frequency domain solution to determining phase may provide information regarding the magnitude or amplitude of the measured transmitted and received magnetic fields. The ratio of the magnitude values can be used to determine the attenuation of the transmitted magnetic field, which may be expressed in logarithmic dB power ratio units.

Alternative Signal Processing in the Time Domain

As one additional alternative signal processing technique in the time domain, the phase shift measurement may be done via one or more relatively low-cost analog phase detectors or by measuring time delays between zero crossings of the transmitted and received wavefield signals. For example, an integrated phase detector circuit may include an amplifier that converts sine waves of transmitted and received wavefields to square waves by clipping the sine waves (e.g., with an extra high gain), and then compares the clipped/square wave from the transmitter with that from the receiver using an analog exclusive OR (XOR) gate, with the pulse width provided by the XOR gate being indicative of the phase shift between the transmitted and received magnetic fields.

Reduction of Phase Measurement Errors Due to Motion

Among all of the factors that contribute to phase measurement error, many are related to motion—motion of the patient, movement of the transmitter 120, movement of the receiver 124, bending of the connection or transmission cables, etc. For example, relative motion between the patient and the transmitter 120/receiver 124 results in path length and location variations for the magnetic field lines as they pass through the patient's head. Conductive or magnetic objects moving near the transmitter 120 and/or near the receiver 124 can also change the shape of the magnetic field lines as they pass from the transmitter 120 to the receiver 124.

In some embodiments, methods may be deployed to reduce artifacts attributable to patient movement. These algorithms may, for example, detect statistical variations in the differential phase shift data across the frequency spectrum of interest (e.g., from about 30 MHz to 300 MHz or about 20 MHz to 200 MHz) that could not possibly be the result of biological changes, as determined by their rates of change or other characteristics. This thresholding-type of method may thus be used to eliminate data corrupted by means other than true biological changes.

As another example, the attenuation data that is obtained from the magnitude portion of the FFT processing can be utilized in algorithms by examining the way it varies across the frequency spectrum to aid in the detection and correction of motion artifacts in the phase shift data.

As still another example, electronic accelerometers can additionally or alternatively be used to detect motion of one or more of the transmitter 120, the receiver 124, the patient, or the transmission cables. In some examples, accelerometers may be coupled to the same printed circuit board as the transmitter or receiver (e.g., using a MEMS type accelerometer).

In addition to detecting any motion above a threshold level, a relationship between the transmitter/receiver accelerometer data and patient accelerometer data may be examined for relative differences. For example, small amplitude changes sensed in both the patient and the transmitter/receiver may be of little consequence. Some patient motion is almost always present (because, e.g., even comatose patients breathe). Larger or non-correlated accelerometer readings, however, may be used to trigger data rejection or correction. Because the separate motion of totally independent objects near the patient can also present motion artifacts in the data then some types of motion detection and correction based on statistical analyses of the phase data may still be required.

Medical Diagnostic Methods for Alerting Clinicians

The system 100 described herein may be used to, among other things, measure the change in phase shift induced by changes in fluid content within, for example, a patient's head ("intracranial fluid"). Methods can be employed to analyze the phase data and make a determination as to whether the fluid change represents a tissue change that is troubling to the clinician user. For example, a baseline reading of the phase shift between a magnetic field transmitted from a transmitter 120 positioned on one side of a patient's head and a magnetic field received at a receiver 124 positioned on the other side of the patient's head at one or more frequencies may be recorded when the patient first arrives at the hospital. Then, any significant changes in the measured phase shift that occurs during subsequent scans can be tracked and trended by clinicians to aid in understanding the patient's clinical condition, and certain thresholds, patterns or trends may trigger an alarm. Many methods may be employed and optimized to provide the clinicians with the most useful fluid change information. For example, if the phase shifts by more than a certain number of degrees, the system may sound an alarm to alert the clinician that the patient may have clinically significant bleeding or edema. For some conditions, it may be useful to alert the clinician if the rate of change of the phase shift exceeds a threshold.

The phase shifts at different frequencies may vary with different fluid changes, as described, for example, U.S. Pat. No. 7,638,341, which is hereby incorporated by reference in its entirety for all purposes. Certain patterns of phase shift may be correlated with certain clinical conditions. For example, a condition such as bleeding or edema may be evidenced by an increase in phase angle at one frequency, with a concurrent decrease at a different frequency. Using ratios of phase shifts at different frequencies can provide additional information about the types of fluids and how they are changing. For example, the ratio of phase shift at a first frequency to the phase shift at a second frequency may be a good parameter to assess blood content or to separate edema from bleeding or other fluid change. For example, the phase shift frequency response of saline may be different from the phase shift frequency response of blood, thus allowing a clinician to separately identify changes in blood and saline content in a patient's brain cavity. Changes in amounts of water may have relatively little effect on phase shift in some instances, although the concentration of electrolytes in an ionic solution may have a more pronounced effect.

The phase shift patterns may also be time dependent. A hypothetical clinical condition may be characterized by an increase in phase shift for some period of time, then stabilizing, and then returning to baseline after some other time period. Noise factors such as patient activities like getting up out of bed, eating, getting blood drawn or speaking with visitors may cause changes to the phase shift readings from baseline. Clinically meaningful fluid changes may be differentiated from noise by examining the patterns associated with different activities.

Using combinations of phase shift data at various frequencies, ratios or other functions of those phase shifts, and/or time-based methods may all be combined and optimized in various embodiments to provide a range of useful information about tissue and/or fluid changes to clinicians. The clinicians can then respond to the tissue changes by using more specific diagnostic techniques such as medical imaging to diagnose a clinical problem.

In some cases, therapies may be changed in response to fluid and/or tissue change information. For example, the diagnostic system described herein may monitor fluid changes in a patient who is on blood thinners to dissolve a clot in a cerebral artery. If the system detects an intracerebral bleed, the blood thinners may be reduced or stopped to help manage the bleeding, or other interventions such as vascular surgery may be performed to stop the bleeding. As another example, a patient who begins to experience cerebral edema may undergo medical interventions to control or reduce the edema, or can undergo surgical procedures to drain fluid or even have a hemicraniectomy to reduce intracerebral pressure due to the edema.

Clinicians may, in some cases, use fluid change information to manage medication dosage by examining what is effectively feedback from the diagnostic system. For example, if mannitol is used to reduce intracerebral pressure by drawing water out of the brain, a treating clinician may use the diagnostic system described herein in order to receive feedback regarding how the patient's brain water is changing in response to the medication.

Similarly, drugs for blood pressure management, electrolyte concentration and other parameters may be more effectively administered when dosage amounts are controlled responsive to feedback from the diagnostic system described herein. For example, cerebral sodium concentrations may be controlled using intravenous hypertonic or hypotonic saline solutions. Changes to the ion concentrations can be detected as a shift in phase angle or some function of shift in phase angle at one or more frequencies. Such information can be used as feedback to the physician to better manage the patient.

Although specific embodiments of the disclosure have been described herein for purposes of illustration, various modifications may be made without deviating from the spirit and scope of the disclosure. For example, although the present application includes several examples of monitoring fluid changes in the human brain as one potential application for the systems and methods described herein, the present disclosure finds broad application in a host of other applications, including monitoring fluid changes in other areas of the human body (e.g., arms, legs, lungs, etc.), in monitoring fluid changes in other animals (e.g., sheep, pigs, cows, etc.), and in other medical diagnostic settings. Fluid changes in an arm, for example, may be detected by having an arm wrapped in a bandage that includes a transmitter and a receiver.

A few examples of the other medical diagnostic settings in which the systems and methods described herein may be used include determining an absolute proportion of a particular fluid, tissue (e.g., muscle, fat, parenchymal organs, etc.), or other solid matter (e.g., a tumor) in a given area of a human body, determining relative permittivity and/or relative permeability of an object, and so forth. Further clinical applications include a wide variety of monitoring and diagnostic uses, including internal bleeding detection, distinction between different types of fluid (e.g. blood, extracellular fluid, intracellular fluid, etc.), assessing edema including cerebral edema as well as lymphedema and lung fluid build-up resulting from such conditions as congestive heart failure. All of these applications and many more may be addressed by various embodiments described herein. Accordingly, the scope of the claims is not limited to the specific examples given herein.

What is claimed is:

1. A device for monitoring changes in a medium in a patient's head, the device comprising:
  a headset, comprising:
    a headband;
    a housing coupled with the headband;
    a processor in the housing;
    a transmitter coupled with the headband and configured to transmit multiple time-varying magnetic fields comprising multiple frequencies that are harmonics of one or more fundamental frequencies, including:
      a first time-varying magnetic field comprising multiple simultaneously transmitted frequencies that are harmonics of a first fundamental frequency; and
      after transmitting the first time-varying magnetic field, a second time-varying magnetic field comprising multiple simultaneously transmitted frequencies that are harmonics of a second fundamental frequency; and
    a receiver coupled with the headset such that it is located on an opposite side of the patient's head from the transmitter when the headset is applied to the patient's head, wherein the receiver is configured to receive the first and second time-varying magnetic fields transmitted by the transmitter;
  wherein the processor is configured to:
    determine at least one of a first phase shift or a first magnitude change between the transmitted first magnetic field and the received first magnetic field;
    determine at least one of a second phase shift or a second magnitude change between the transmitted second magnetic field and the received second magnetic field;
    generate a comparison of the second phase shift to the first phase shift or the second magnitude change to the first magnitude change, for a plurality of the multiple frequencies; and
    determine, based on the comparison, whether a change in the medium in the patient's head has occurred.

2. The device of claim 1, further comprising an accelerometer attached to the headset for detecting motion of the patient, wherein the processor is further configured to distinguish the comparison from the detected motion.

3. The device of claim 1, wherein the headband is disposable and the processor is reusable.

4. The device of claim 1, wherein the headband comprises a material selected from a group consisting of elastic, rubber, acrylic, latex and other flexible materials.

5. The device of claim 1, wherein the receiver is housed in the housing.

6. The device of claim 1, wherein the processor is further configured to:
- determine that the change in the medium in the patient's head comprises a clinically significant change; and
- generate a signal to alert a user that the clinically significant change has occurred.

7. The device of claim 1, wherein the transmitter is configured to transmit the first and second time-varying magnetic fields in a frequency range of 20 MHz to 300 MHz.

8. The device of claim 1, wherein the medium in the patient's head comprises fluid in the patient's brain.

9. The device of claim 1, wherein the first fundamental frequency and the second fundamental frequency are the same.

* * * * *